United States Patent [19]

Bock et al.

[11] Patent Number: 4,755,508
[45] Date of Patent: Jul. 5, 1988

[54] BENZODIAZEPINE ANALOGS AND USE AS ANTOGONISTS OF GASTRIN AND CHOLECYSTOKININ

[75] Inventors: Mark G. Bock, Hatfield; Ben E. Evans, Lansdale; Roger M. Freidinger, Hatfield, all of Pa.

[73] Assignee: Merck & Co., Inc., Rahway, N.J.

[21] Appl. No.: 20,261

[22] Filed: Feb. 27, 1987

Related U.S. Application Data

[63] Continuation-in-part of Ser. No. 741,973, Jul. 10, 1985, abandoned, which is a continuation-in-part of Ser. No. 624,852, Jun. 26, 1984, abandoned.

[51] Int. Cl.$^4$ .................... A61K 31/55; C07D 243/20; C07D 243/16
[52] U.S. Cl. .................... 514/221; 540/542; 540/570; 540/571; 540/572
[58] Field of Search ................ 514/221; 540/542, 570, 540/571, 572

[56] References Cited

U.S. PATENT DOCUMENTS

| | | | |
|---|---|---|---|
| 3,320,239 | 5/1967 | Stempel et al. | 540/571 |
| 3,795,673 | 3/1974 | Meguro et al. | 260/239 BD X |
| 4,089,953 | 5/1978 | Shenoy | 260/239 BD X |
| 4,102,881 | 7/1978 | Tawada et al. | 260/239 BD |
| 4,395,409 | 7/1983 | Försch et al. | 514/221 |

OTHER PUBLICATIONS

J. Heterocyclic Chem., 17, 865 (1980) Gatta et al., pp. 865–868.
Allgeier et al., Chemical Abstracts, vol. 78 (1973) 29832u.
Allgeier et al., Chemical Abstracts, vol. 85 (1976) 108681s.
Watanabe et al., Chemical Abstracts, vol. 97 (1982) 92240g.
Giacconi et al., Synthesis, (1982) pp. 789–791.
Natsugari et al., Chem. Pharm. Bull., vol. 27 (1979) pp. 2608–2617.
Schecker et al., Arch. Pharm., 313 (1980) pp. 926–936.

*Primary Examiner*—Richard L. Raymond
*Attorney, Agent, or Firm*—R. D. Meredith; H. J. Pfeiffer; S. B. Abrams

[57] ABSTRACT

Benzodiazepines of the formula:

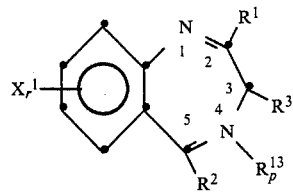

are disclosed which are antagonists of gastrin and cholecystokinin (CCK).

9 Claims, No Drawings

BENZODIAZEPINE ANALOGS AND USE AS ANTOGONISTS OF GASTRIN AND CHOLECYSTOKININ

The present application is a continuation-in-part of U.S. patent application Ser. No. 741,973, filed July 10, 1985, now abandoned, which in turn is a continuation-in-part of U.S. patent application Ser. No. 624,852, filed June 26, 1984, now abandoned.

BACKGROUND OF THE INVENTION

The benzodiazepines (Formula IV) which are the starting materials for the compounds of Formula I are described in U.S. patent application, Ser. No. 741,972, filed June 10, 1985, now abandoned, which is a continuation-in-part of U.S. patent application, Ser. No. 705,272, filed Feb. 25, 1985, now abandoned, which in turn is a continuation-in-part of U.S. patent application, Ser. No. 624,854, filed June 26, 1984, now abandoned.

Cholecystokinins (CCK) and gastrin are structurally-related neuropeptides which exist in gastrointestinal tissue and in the the central nervous system (see, V. Mutt, *Gastrointestinal Hormones*, G. B. J. Glass, Ed., Raven Press, N.Y., p. 169 and G. Nisson, ibid, p. 127).

Cholecystokinins include CCK-33, a neuropeptide of thirty-three amino acids in its originally isolated form (see, Mutt and Jorpes, *Biochem. J.* 125, 678 (1971)), its carboxylterminal octapeptide, CCK-8 (a naturally-occurring neuropeptide, also, and the minimum fully active sequence), and 39- and 12-amino acid forms, while gastrin occurs in 34-, 17- and 14-amino acid forms, with the minimum active sequence being the C-terminal pentapeptide, Gly-Trp-Met-Asp-Phe-$NH_2$, which is the common structural element shared by both CCK and gastrin.

CCK's are believed to be physiological satiety hormones, thereby possibly playing an important role in appetite regulation (G. P. Smith, *Eating and Its Disorders*, A. J. Stunkard and E. Stellar, Eds, Raven Press, New York, 1984, p. 67), as well as also stimulating colonic motility, gall bladder contraction, pancreatic enzyme secretion, and inhibiting gastric emptying. They reportedly co-exist with dopamine in certain mid-brain neurons and thus may also play a role in the functioning of dopaminergic systems in the brain, in addition to serving as neurotransmitters in their own right (see: A. J. Prange et al., "Peptides in the Central Nervous System", *Ann. Repts. Med. Chem.* 17, 31, 33 [1982] and references cited therein; J. A. Williams, Biomed. Res. 3 107 [1982]); and J. E. Morley, Life Sci. 30, 479, [1982]).

The primary role of gastrin, on the other hand, appears to be stimulation of the secretion of water and electrolytes from the stomach, and, as such, it is involved in control of gastric acid and pepsin secretion. Other physiological effects of gastrin then include increased mucosal blood flow and increased antral motility, with rat studies having shown that gastrin has a positive tropic effect on the gastric mucosa, as evidenced by increased DNA, RNA and protein synthesis.

Antagonists to CCK and to gastrin have been useful for preventing and treating CCK-related and/or gastrin-related disorders of the gastrointestinal (GI) and central nervous (CNS) systems of animals, especially of humans. Just as there is some overlap in the biological activities of CCK and gastrin, antagonists also tend to have affinity for both receptors. In a practical sense, however, there is enough selectivity to the different receptors that greater activity against specific CCK- or gastrin-related disorders can often also be identified.

Selective CCK antagonists are themselves useful in treating CCK-related disorders of the appetite regulatory systems of animals as well as in potentiating and prolonging opiate-mediated analgesis, thus having utility in the treatment of pain [see P. L. Faris et al., Science 226, 1215 (1984)], while selective gastrin antagonists are useful in the modulation of CNS behavior, as a palliative for gastrointestinal neoplasms, and in the treatment and prevention of gastrin-related disorders of the gastrointestinal system in humans and animals, such as peptic ulcers, Zollinger-Ellison syndrome, antral G cell hyperplasia and other conditions in which reduced gastrin activity is of therapeutic value.

Also, since CCK and gastrin also have trophic effects on certain tumors [K. Okyama, *Hokkaido J. Med. Sci.*, 60, 206–216 (1985)], antagonists of CCK and gastrin are useful in treating these tumors [see, R. D. Beauchamp et al., *Ann. Surg.*, 202,303 (1985)].

Four distinct chemical classes of CCK-receptor antagonists have been reported. The first class comprises derivatives of cyclic nucleotides, of which dibutyryl cyclic GMP has been shown to be the most potent by detailed structure-function studies (see, N. Barlos et al., *Am. J. Physiol.*, 242, G 161 (1982) and P. Robberecht et al., *Mol., Pharmacol.*, 17, 268 (1980)).

The second class comprises peptide antagonists which are C-terminal fragments and analogs of CCK, of which both shorter (Boc-Met-Asp-Phe-$NH_2$, Met-Asp-Phe-$NH_2$), and longer (Cbz-Tyr($SO_3H$)-Met-Gly-Trp-Met-Asp-$NH_2$) C-terminal fragments of CCK can function as CCK antagonists, according to recent structure-function studies (see, R. T. Jensen et al., *Biochem. Biophys. Acta*, 757, 250 (1983),and M. Spanarkel et al., *J. Biol. Chem.*, 258, 6746 (1983)). The latter compound was recently reported to be a partial agonist [see, J. M. Howard et al., *Gastroenterology* 86(5) Part 2, 1118 (1984)].

Then, the third class of CCK-receptor antagonists comprises the amino acid derivatives: proglumide, a derivative of glutaramic acid, and the N-acyl tryptophans including para-chlorobenzoyl-L-tryptophan (benzotript), [see, W. F. Hahne et al., *Proc. Natl. Acad. Sci. U.S.A.*, 78, 6304 (1981), R. T. Jensen et al., *Biochem. Biophys. Acta.*, 761, 269 (1983)]. All of these compounds, however, are relatively weak antagonists of CCK ($IC_{50}$: generally $10^{-4}$M [although more potent analogs of proglumide have been recently reported in F. Makovec et al., *Arzneim-Forsch Drug Res.*, 35 (II), 1048 (1985) and in German Patent Application DE No. 3522506A], but down to $10^{-6}$M in the case of peptides), and the peptide CCK-antagonists have substantial stability and absorption problems.

In addition, a fourth class consists of improved CCK-antagonists comprising a nonpeptide of novel structure from fermentation sources [R. S. L. Chang et al., *Science*, 230, 177–179 (1985)] and 3-substituted benzodiazepines based on this structure [published European Patent Applications Nos. 167 919, 167 920 and 169 392, B. E. Evans et al, *Proc. Natl. Acad. Sci. U.S.A.*, 83, p. 4918–4922 (1986) and R. S. L. Chang et al, ibid, p. 4923–4926] have also been reported.

No really effective receptor antagonists of the in vivo effects of gastrin have been reported (J. S. Morley, *Gut Pept. Ulcer Proc.*, Hiroshima Symp. 2nd, 1983, p. 1), and very weak in vitro antagonists, such as proglumide and certain peptides have been described [(J. Martinez, *J.*

Med. Chem. 27, 1597 (1984)]. Recently, however, pseudopeptide analogs of tetragastrin have been reported to be more effective gastrin antagonists than previous agents [J. Martinez et al., J. Med. Chem., 28, 1874–1879 (1985)].

The benzodiazepine (BZD) structure class, which has been widely exploited as therapeutic agents, especially as central nervous system (CNS) drugs, such as anxiolitics, and which exhibits strong binding to "benzodiazepine receptors" in vitro, has not in the past been reported to bind to CCK or gastrin receptors. Benzodiazepines have been shown to antagonize CCK-induced activation of rat hippocampal neurones but this effect is mediated by the benzodiazepine receptor, not the CCK receptor [see J. Bradwejn et al., Nature, 312, 363 (1984)]. Of these reported BZD's, additionally, the large majority do not contain substituents attached to the 3-position of the seven membered ring, as it is well known in the art that 3-substituents result in decreasing anxiolitic activity, especially as these substituents increase in size. Further, it has been demonstrated that in the case of the 3-substituted benzodiazepines that have been reported, the preferred stereochemistry at position 3 for CNS activity is S, which would correspond to an L-amino acid, such as L-tryptophan.

It was, therefore, an object of this invention to identify substances which more effectively antagonize the function of cholecystokinins and gastrin in disease states in animals, preferably mammals, especially in humans. It was another object of this invention to prepare novel compounds which more selectively inhibit cholecystokinins or inhibit gastrin. It was still another object of this invention to develop a method of antagonizing the functions of cholecystokinin and gastrin in disease states in mammals. It is also an object of this invention to develop a method of preventing or treating disorders of the gastrointestinal, central nervous and appetite regulatory systems of mammals, especially of humans, or of increasing food intake of animals.

SUMMARY OF THE INVENTION

It has now been found that compounds of Formula I are antagonists of gastrin and cholecystokinin (CCK). These gastrin and CCK antagonists are useful in the treatment and prevention of gastrin and CCK-related disorders of the gastrointestinal, central nervous and appetite regulatory systems of mammals, especially humans. The compounds of Formula I are also gastrin antagonists. They are useful in the treatment and prevention of gastrointestinal ulcers, Zollinger-Ellison syndrome, antral G cell hyperplasia, and other conditions in which reduced gastrin activity is of therapeutic value.

DETAILED DESCRIPTION OF THE INVENTION

The compounds of this invention are those of Formula I:

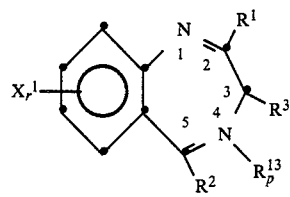

wherein
$R^1$ is $-NR^{16}R^{17}$;
$R^2$ is H, loweralkyl, substituted or unsubstituted phenyl (wherein the substituents are 1 or 2 of halo, loweralkyl, loweralkoxy, lower-alkylthio, carboxyl, carboxyloweralkyl, nitro, $-CF_3$, or hydroxy), 2-, 3-, 4-pyridyl,

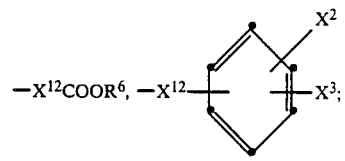

$R^3$ is

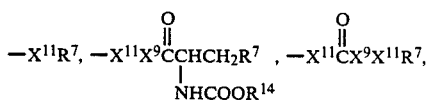

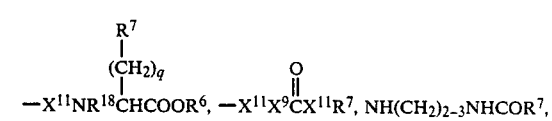

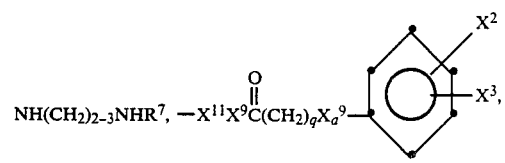

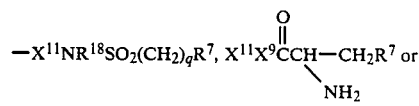

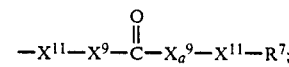

$R^4$ and $R^5$ are independently $R^6$ or in combination with the N of the $NR^4R^5$ group form an unsubstituted or mono or disubstituted, saturated or unsaturated, 4–7 membered heterocyclic ring, or benzofused 4–7 membered heterocyclic ring or said heterocyclic ring or said benzofused heterocyclic ring which further comprises a second heteroatom selected from O and $NCH_3$ and the substituent(s) is/are independently selected from $C_{1-4}$alkyl;

$R^6$ is H, loweralkyl, cycloloweralkyl, substituted or unsubstituted phenyl, or substituted or unsubstituted phenylloweralkyl (wherein the substituents are 1 or 2 of halo, loweralkyl, loweralkoxy, nitro, or $CF_3$);

$R^7$ is α- or β-naphthyl, substituted or unsubstituted phenyl (wherein the substituents are 1 to 2 of halo, $-NO_2$, $-OH$, $-X^{11}-NR^4R^5$, loweralkyl, loweralkoxy, $CF_3$, loweralkylthio, cyano, phenyl, acetylamino, acetoxy, $SCF_3$, $C\equiv CH$, $CH_2SCF_3$, $OCHF_2$, SH or thio-phenyl) 2-, 3-, 4pyridyl

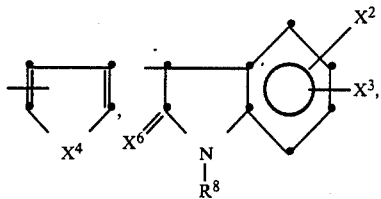

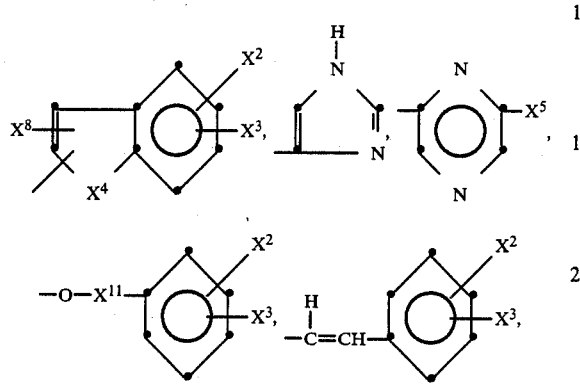

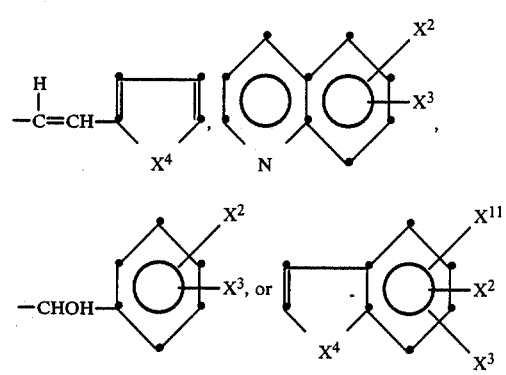

(with the proviso that q is not 0 in $-X^{11}NR^{18}CHCOOR_6$ when $R^7$ is $-O-X^{11}-$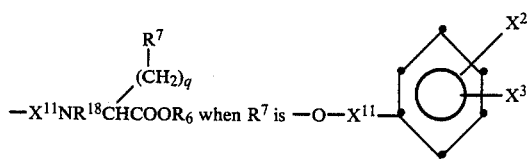

$R^8$ is H, loweralkyl, cycloloweralkyl, $-X^{12}CONH_2$, $-X^{12}COOR^6$, $-X^{11}$-cycloloweralkyl, $-X^{12}NR^4R^5$,

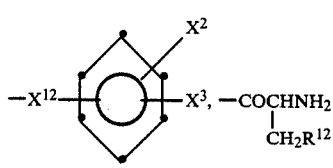, $-COCHNH_2$ | $CH_2R^{12}$ $-X^{11}CO(CH_2)_q$ 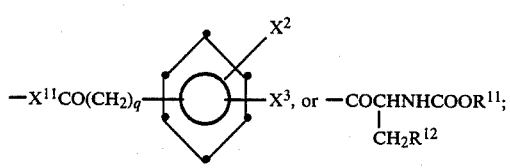, or $-COCHNHCOOR^{11}$; | $CH_2R^{12}$ $R^{11}$ and $R^{12}$ are independently loweralkyl or cycloloweralkyl;

$R^{13}$ is O;

$R^{14}$ is loweralkyl or phenylloweralkyl;

$R^{16}$ and $R^{17}$ are, when separate, independently H, loweralkyl, lower alkenyl, —$X^{11}$ cycloloweralkyl, —$X^{12}$—$NR^4R^5$, $X^{12}CONR^4R^5$, —$X^{12}C\equiv N$,

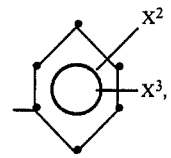

—$X^{12}COOR^6$, or —CN; or, when joined, form with N, a heterocycle

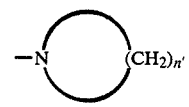

wherein n' is 2–6;

$R^{18}$ is H or loweralkyl;

p is 0 or 1;

q is 0–4;

r is 1 or 2;

$X^1$ is H, —$NO_2$, $CF_3CN$, OH, loweralkyl, halo, loweralkylthio, loweralkoxy, —$X^{11}COOR^6$ or —$X^{11}NR^4R^5$;

$X^2$ and $X^3$ are independently H, —OH, —$NO_2$, halo, loweralkylthio, loweralkyl or loweralkoxy;

$X^4$ is S, O, $CH_2$ or $NR^8$;

$X^5$ is H, $CF_3$, CN, $COOR^6$, $NO_2$, or halo;

$X^6$ is O or HH;

$X^8$ is H or loweralkyl;

$X^9$ and $X^9$ are independently $NR^{18}$, O;

$X^{11}$ is absent or $C_{1-4}$ linear or branched alkylidene;

$X^{12}$ is $C_{1-4}$ linear or branched alkylidene and the pharmaceutically acceptable salts thereof.

In the compounds of Formula I, the preferred stereochemistry relates to D-tryptophan, where $C^2$ and $N^4$ of Formula I correspond to the carbonyl carbon and α-amino nitrogen of D-tryptophan and $R^3$ occupies the position of the indolylmethyl side chain.

As used herein, the definition of each expression, e.g. p, loweralkyl, etc., when it occurs more than once in any structure, is intended to be independent of its definition elsewhere in the same structure.

As used herein, halo is F, Cl, Br or I; loweralkyl is 1–6 carbon straight or branched chain alkyl and includes methyl, ethyl, propyl, isopropyl, butyl, isobutyl, t-butyl, pentyl, and hexyl; in loweralkoxy and loweralkylthio, the alkyl portion is loweralkyl as previously defined; cycloloweralkyl is cycloalkyl of 3–5 carbons; and acyl is formyl, acetyl, propionyl, or butyryl.

The pharmaceutically acceptable salts of the compounds of Formulas I include the conventional non-toxic salts or the quaternary ammonium salts of the compounds of Formula I formed, e.g., from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicyclic, sulfanilic, 2-acetoxybenzoic, fumaric, toluenesulfonic, methanesulfonic, ethane disulfonic, oxalic, isethionic, and the like.

The pharmaceutically acceptable salts of the present invention can be synthesized from the compounds of Formula I which contain a basic or acidic moiety by conventional chemical methods. Generally, the salts are prepared by reacting the free base or acid with stoichiometric amounts or with an excess of the desired salt forming inorganic or organic acid or base in a suitable solvent or various combinations of solvents.

The pharmaceutically acceptable salts of the acid of Formula I are also readily prepared by conventional procedures such as treating an acid of Formula I with an appropriate amount of a base, such as an alkali or alkaline earth metal hydroxide e.g. sodium, potassium, lithium, calcium, or magnesium, or an organic base such as an amine, e.g., dibenzylethylenediamine, trimethylamine, piperidine, pyrrolidine, benzylamine and the like, or a quaternary ammonium hydroxide such as tetramethylammonium hydroxide and the like.

An embodiment of this invention is the preparation of compounds of Formula I.

Another embodiment is the use of the compounds of Formula I for the treatment and the prevention of disorders of the gastrointestinal, central nervous, and appetite regulatory systems of mammals, especially of man. Specifically, the Formula I compounds are useful in treatment and prevention of disorders of gastric acid secretion, gastrointestinal motility, pancreatic secretions, and dopaminergtic functions. The compounds of Formula I are especially useful in the prevention and treatment of irritable bowel syndrome.

A further embodiment is a composition comprising an effective amount of a compound of Formula I and a pharmaceutically acceptable carrier.

The ability of the compounds of Formula I to antagonize CCK and gastrin makes these compounds useful as pharmaceutical agents for mammals, especially for humans, for the treatment and prevention of disorders wherein CCK and/or gastrin may be involved. Examples of such disease states include gastrointestinal disorders, especially such as irritable bowel syndrome or ulcers, excess pancreatic or gastric secretion, acute pancreatis, or motility disorders; central nervous system disorders, caused by CCK interactions with dopamine, such as neuroleptic disorders, tardive dyskinesia, Parkinson's disease, psychosis or Gilles de la Tourette Syndrome; disorders of appetite regulatory systems; Zollinger-Ellison syndrome, antral G cell hyperplasia, or pain (potentiation of opiate analgesia); as well as certain tumors of the lower esophagus, stomach, intestines and colon.

The compounds of Formula I thereof, may be administered to a human subject either alone or, preferably, in combination with pharmaceutically-acceptable carriers or diluents, optionally with known adjuvants, such as alum, in a pharmaceutical composition, according to standard pharmaceutical practice. The compounds can be administered orally or parenterally, including intravenous, intramuscular, intraperitoneal, subcutaneous and topical administration.

For oral use of an antagonist of CCK, according to this invention, the selected compounds may be administered, for example, in the form of tablets or capsules, or as an aqueous solution or suspension. In the case of tablets for oral use, carriers which are commonly used include lactose and corn starch, and lubricating agents, such as magnesium stearate, are commonly added. For oral administration in capsule form, useful diluents include lactose and dried corn starch. When aqueous suspensions are required for oral use, the active ingredient is combined with emulsifying and suspending agents. If desired, certain sweetening and/or flavoring agents may be added. For intramuscular, intraperitoneal, subcutaneous and intravenous use, sterile solutions of the active ingredient are usually prepared, and the pH of the solutions should be suitably adjusted and buffered. For intravenous use, the total concentration of solutes should be controlled in order to render the preparation isotonic.

When a compound according to Formula I is used as an antagonist of CCK or gastrin in a human subject, the daily dosage will normally be determined by the prescribing physician with the dosage generally varying according to the age, weight, and response of the individual patient, as well as the severity of the patient's symptoms. However, in most instances, an effective daily dosage will be in the range of from about 0.05 mg/kg to about 50 mg/kg of body weight, and preferably, of from 0.5 mg/kg to about 20 mg/kg of body weight, administered in single or divided doses. In some cases, however, it may be necessary to use dosages outside these limits.

In the treatment of irritable bowel syndrome, for instance, 0.1 to 10 mg/kg of a CCK antagonist might be administered orally (p.o.), divided into two doses per day (b.i.d.). In treating delayed gastric emptying, the dosage range would probably be the same, although the drug might be administered either intravenously (I.V.) or orally, with the I.V. dose probably tending to be slightly lower due to better availability. Acute pancreatitis might be treated preferentially in an I.V. form, whereas spasm and/or reflex esophageal, chronic pancreatitis, past vagatomy diarrhea, or treatment of anorexia or of pain associated with biliary dyskinesia might indicate p.o. form administration.

In the use of a gastrin antagonist as a tumor palliative for gastrointestinal neoplasms with gastrin receptors, as a modulator of central nervous system activity treatment of Zollinger-Ellison syndrome, or in the treatment of peptic ulcer disease, a dosage of 0.1 to 10 mg/kg administered one-to-four times daily might be indicated.

Because these compounds antagonize the function of CCK in animals, they may also be used as feed additives to increase the food intake of animals in daily dosage of approximately 0.05 to 50 mg/kg of body weight.

The compounds of Formula I are prepared according to the following scheme.

REACTION SCHEME I

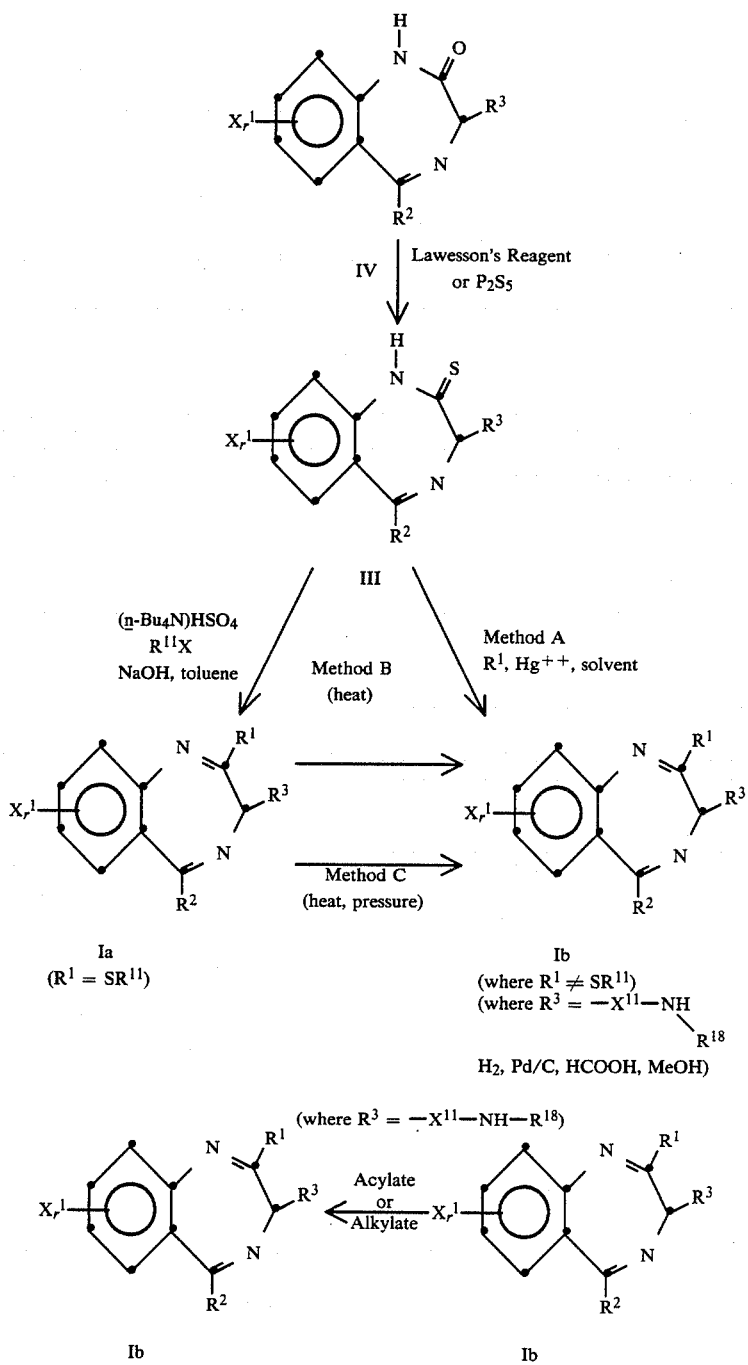

Referring to Scheme I, the compounds of Formula I are prepared as follows: 1,3-Dihydro-3,5-disubstituted-1,4-benzodiazepines IV are reacted with phosphorus pentasulfide or preferably Lawesson's reagent (2,4-bis-(4-methoxyphenyl)-2,4-dithioxo-1,3,2,4-dithiadiphosphetane) in an aprotic solvent, preferably toluene at room temperature to the boiling point of the solvent, to give the corresponding thioamides III.

Treatment of the benzodiazepin-2-thiones III with an alcohol or an amine in a solvent, preferably tetrahydrofuran, in the presence of a mercury salt such as mercuric chloride or mercuric acetate affords the title compound Ib, (Method A).

Alternatively, the benzodiazepin-2-thiones III can be converted to the title compound thioiminoethers Ia with an alkylating agent, preferably a lower alkyl halide or cycloloweralkyl halide, at room temperature, under phase transfer conditions requiring aqueous base, such as an alkali earth hydroxide, an organic solvent immiscible with water, preferably toluene and a catalyst, preferably, tetra-n-butylammonium hydrogen sulfate. The thioiminoethers Ia are, in turn, transformed to the title compounds Ib by reaction with an amine or alcohol for 2-96 hours preferably 24 hours, at room temperature to the boiling point of the reagent, preferably 80° C., (Method B). Compounds of formula Ib are also accessible by heating iminoethers Ia with an amine or alcohol in a sealed pressure vessel at 80°-250° C., preferably 120°, for 1-36 hours, preferably 12 hours, (Method C).

When $R^3$ in compounds of Formula IV contains an amino, keto, or alcohol moiety, this moiety should be protected during the synthesis of Ia or Ib according to methods known in the art. Removal of such protecting groups according to methods known in the art at the end the synthesis provides Ia or Ib.

For the case of $R^3$ containing a funtionalized amino group, Scheme I is performed on IV,

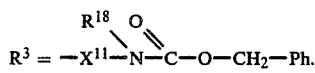

The protecting group is then removed from Ib by catalytic transfer hydrogenolysis, and the resultant amine [Ib, $R^3 = -X^{12}-NH-R^{18}$] is derivatized appropriately, e.g. with an acid $HOOC-(CH_2)_q-R^7$ to give Ib,

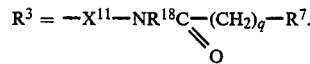

In cases where the starting materials are optically active, the chirality at $C_3$ is controlled by the synthesis. When racemic starting materials are employed, racemic mixtures are obtained. The enantiomers may be separated by resolution.

IN VITRO ACTIVITY OF FORMULA I

The biological activity of the compounds of Formula I have been evaluated using (1) an $^{125}$I-CCK receptor binding assay and in vitro isolated tissue preparations and (2) $^{125}$I-gastrin and $^3$H-pentagastrin binding assays.

MATERIALS AND METHODS

1. CCK Receptor Binding (Pancreas)

CCK-33 was radiolabeled with $^{125}$I-Bolton Hunter reagent (2000 Ci/mmole) as described by Sankara et al. (*J. Biol. Chem.* 254: 9349-9351, 1979). Receptor binding was performed according to Innis and Snyder (*Proc. Natl. Acad. Sci.* 77: 6917-6921, 1980) with the minor modification of adding the additional protease inhibitors, phenylmethane sulfonyl fluoride and o-phenanthroline. The latter two compounds have no effect on the $^{125}$I-CCK receptor binding assay.

Male Sprague-Dawley rats (200-350 g) were sacrificed by decapitation. The whole pancreas was dissected free of fat tissue and was homogenized in 20 volumes of ice-cold 50 mM, Tris HCl (pH 7.7 at 25° C.) with a Brinkmann Polytron PT 10. The homogenates were centrifuged at 48,000 g for 10 min. Pellets were resuspended in Tris Buffer, centrifuged as above and resuspended in 200 volumes of binding assay buffer (50 mM Tris HCl, pH 7.7 at 25° C., 5 mM dithiothrietol, 0.1 mM bacitracin, 1.2 mM phenylmethane sulfonyl fluoride and 0.5 mM o-phenanthroline). For the binding assay, 25 μl of buffer (for total binding) or unlabeled CCK-8 sulfate to give a final concentration of 1 μM (for nonspecific binding) or the compounds of Formula I (for determination of inhibition of $^{125}$I-CCK binding) and 25 μl of $^{125}$I-CCK-33 (30,000-40,000 cpm) were added to 450 μl of the membrane suspensions in microfuge tubes. All assays were run in duplicate or triplicate. The reaction mixtures were incubated at 37° C. for 30 minutes and centrifuged in a Beckman Microfuge (4 minutes) immediately after adding 1 ml of ice-cold incubation buffer. The supernatant was aspirated and discarded, pellets were counted with a Beckman gamma 5000. For Scatchard analysis (*Ann. N.Y. Acad. Sci.* 51: 660, 1949), $^{125}$I-CCK-33 was progressively diluted with increasing concentrations of CCK-33

2. CCK Receptor Binding (Brain)

CCK-33 was radiolabeled and the binding was performed according to the description for the pancreas method with modifications according to Saito et al., *J. Neurochem.* 37, 483-490, 1981.

Male Hartley guinea pigs (300-500 g) were sacrificed by decapitation and the brains were removed and placed in ice-cold 50 mM, Tris HCl plus 7.58 g/l Trizma-7.4 (pH 7.4 at 25° C.). Cerebral cortex was dissected and used as a receptor source. Each gram of fresh guinea pig brain tissue was homogenized in 10 ml of Tris Trizma buffer with a Brinkman polytron PT-10. The homogenates were centrifuged at 42,000 g for 15 min. Pellets were resuspended in Tris Buffer, centrifuged as above and resuspended in 200 volumes of binding assay buffer (10 mM N-2-hydroxethyl-piperazine-N'-2-ethane sulfonic acid (HEPES), 5 mM $MgCl_2$, 0.25 mg/ml bacitracin, 1 mM ethylene glycol-bis-(β-aminoethyl-ether-N,N'-tetraacetic acid (EGTA), and 0.4% bovine serum albumin (BSA)). For the binding assay, 25 μl of buffer (for total binding) or unlabeled CCK-8 sulfate to give a final concentration of 1 μM (for nonspecific binding) or the compounds of Formula I (for determination of inhibition of $^{125}$I-CCK binding) and 25 μl of $^{125}$I-CCK-33 (30,000-40,000 cpm) were added to 450 μl of the membrane suspensions in microfuge tubes. All assays were run in duplicate or triplicate. The reaction mixtures were incubated at 25° C. for 2 hours and centrifuged in a Beckman Microfuge (4 minutes) immediately after adding 1 ml of ice-cold incubation buffer. The supernatant was aspirated and discarded, pellets were counted with a Beckman gamma 5000.

The compounds of Formula I can be determined to be competitive antagonists of CCK according to the followig assays.

3. Isolated guinea pig gall bladder

Male Hartley guinea pigs (400-600 g) are sacrificed by decapitation. The whole gall bladder is dissected free from adjacent tissues and cut into two equal halves. The gall bladder strips are suspended along the axis of the bile duct in a 5 ml organ bath under 1 g tension. The organ bath contains a Kreb's bicarbonate solution (NaCl 118 mM, KCl 4.75 mM, CaCl 2.54 mM, $KH_2PO_4$ 1.19 mM, Mg $SO_4$ 1.2 mM, $NaHCO_3$ 25 mM and dextrose 11 mM) maintained at 32° C. and bubbled with 95% $O_2$ and 5% $CO_2$. Isometric contractions are recorded using Statham (60 g; 0.12 mm) strain gauges and a Hewlett-Packard (77588) recorder. The tissues are washed every 10 minutes for 1 hr to obtain equilibrium prior to the beginning of the study. CCK-8 is added cumulatively to the baths and $EC_{50}$'s determined using regression analysis. After washout (every 10 minutes for 1 hr), the compound of Formula I is added at least 5 minutes before the addition of CCK-8 and the $EC_{50}$ of CCK-8 in the presence of the compound of Formula I similarly determined.

4. Isolated longitudinal muscle of guinea pig ileum

Longitudinal muscle strips with attached nerve plexus are prepared as described in Brit J. Pharmac. 23:; 356-363, 1964; J. Physiol. 194: 13-33, 1969. Male Hartley guinea pigs are decapitated and the ileum removed (10 cm of the terminal ileum is discarded and the adjacent 20 cm piece used). A piece (10 cm) of the ileum is stretched on a glass pipette. Using a cotton applicator to stroke tangentially away from the mesentery attachment at one end, the longitudinal muscle is separated from the underlying circular muscle. The longitudinal muscle is then tied to a thread and by gently pulling, stripped away from the entire muscle. A piece of approximately 2 cm is suspended in 5 ml organ bath containing Krebs solution and bubbled with 95% $O_2$ and 5% $CO_2$ at 37° C. under 0.5 g tension. CCK-8 is added cumulatively to the baths and $EC_{50}$ values in the presence and absence of compounds of Formula I determined as described in the gall bladder protocol (above).

5. Gastrin Antagonism

Gastrin antagonist activity of compounds of Formula I is determined using the following assay:

GASTRIN RECEPTOR BINDING IN GUINEA PIG GASTRIC GLANDS

PREPARATION OF GUINEA PIG GASTRIC MUCOSAL GLANDS

Guinea pig gastric mucosal glands were prepared by the procedure of Berglingh and Obrink Acta Physiol. Scand. 96: 150 (1976) with a slight modification according to Praissman et al. C. J. Receptor Res. 3: (1983). Gastric mucosa from guinea pigs (300-500 g body weight, male Hartley) were washed thoroughly and minced with fine scissors in standard buffer consisting of the following: 130 mM NaCl, 12 mM $NaHCO_3$, 3 mM $NaH_2PO_4$, 3 mM $Na_2HPO_4$, 3 mM $K_2HPO_4$, 2 mM $MgSO_4$, 1 mM $CaCl_2$, 5 mM glucose and 4 mM L-glutamine, 25 mM HEPES at pH 7.4. The minced tissues were washed and then incubated in a 37° C. shaker bath for 40 minutes with the buffer containing 0.1% collagenase and 0.1% BSA and bubbled with 95% $O_2$ and 5% $CO_2$. The tissues were passed twice through a 5 ml glass syringe to liberate the gastric glands, and then filtered through 200 mesh nylon. The filtered glands were centrifuged at 270 g for 5 minutes and washed twice by resuspension and centrifugation.

IN VITRO RESULTS

1. Effect of The Compounds of Formula I on $^{125}$I-CCK-33 receptor binding

The preferred compounds of Formula I are those which inhibited specific $^{125}$I-CCK-33 binding in a concentration dependent manner.

Scatchard analysis of specific $^{125}$I-CCK-33 receptor binding in the absence and presence of the compounds of Formula I indicated the compound of Formula I competitively inhibited specific $^{125}$I-CCK-33 receptor binding since it increased the $K_D$ (dissociation constant) without affecting the $B_{max}$ (maximum receptor number). A $K_i$ value (dissociation constant of inhibitor) of the compounds of Formula I was estimated.

The data of Table 1 were obtained for compounds of the following structure:

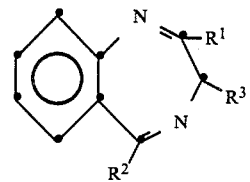

TABLE 1

| | | | | RECEPTOR BINDING RESULTS | | |
|---|---|---|---|---|---|---|
| | | | | $IC_{50}$ (uM) | | |
| Example | $R^1$ | $R^2$ | $R^3$ | $^{125}$I-CCK Pancreas | $^{125}$I-CCK Brain | Gastrin |
| 1 | PhNH | o-F—Ph | 3-indolylmethyl | 34 | 100 | — |
| 2 | $CH_3S$ | o-F—Ph | 3-indolylmethyl | 17 | — | — |
| 3 | $NH_2$ | o-F—Ph | 3-indolylmethyl | 1.7 | — | — |
| 4 | $CH_3NH$ | o-F—Ph | 3-indolylmethyl | 4.5 | >100 | 67 |
| 5 | $CH_3CH_2O_2CNH$ | o-F—Ph | 3-indolylmethyl | 23 | 49 | — |
| 6 | NC—NH | o-F—Ph | 3-indolylmethyl | 2.0 | 100 | — |
| 7 | $CH_3CH_2CH_2NH$ | o-F—Ph | 3-indolylmethyl | 2.7 | >100 | — |
| 8 | $HO_2C—CH_2NH$ | o-F—Ph | 3-indolylmethyl | 3.6 | 31 | 2.7 |
| 9 | $HO_2C—CH_2NH$ | Ph | NHCNH—⟨Ph⟩—Cl (O=) | 0.069 | 0.11 | 0.032 |
| 10 | $CH_3CH_2O_2C—CH_2NH$ | Ph | NHCNH—⟨Ph⟩—Cl (O=) | 1.4 | 0.27 | 0.26 |

Preferred compounds of Formula I are those where $R^1$ is —$NH_2$, —NH$(CH_2)_{0-2}$—$CH_3$, NH—$(CH_2)_{1-2}$—COOH, —NHCN,

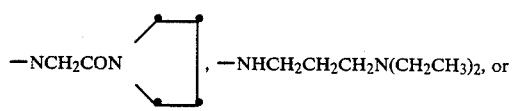

, —$NHCH_2CH_2CH_2N(CH_2CH_3)_2$, or

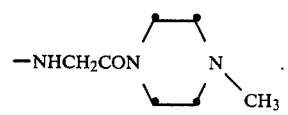

Other series of preferred compounds are those wherein $R^2$ is phenyl, p-chlorophenyl, o-chlorophenyl, o-fluorophenyl, 2,4-dichlorophenyl, 2,6-difluorophenyl, —$CH_2COO$-t-butyl, or —$CH_2COOEt$.

Other series of preferred compounds are those where $R^3$ is 2- or 3-indolylmethyl; NHCO—$R^7$ where $R^7$ is 2-indolyl, 2-(1-methylindolyl), 2-(5-fluoroindolyl), 2-benzofuranyl, 2-benzothienyl, 2-(3-methylindenyl), phenylethenyl, mono- or dihalophenyl, mono- or dimethyl or trifluoromethylphenyl; NHCONH-p-chlorophenyl, NHCONH-m-methylphenyl, NHCONH-p-methylphenyl, or NHCONH-m-methoxyphenyl.

It is preferred that $X_r^1$ is H, Cl, F, $CF_3$, OH or $NO_2$.

Examples of Formula I compounds are tabulated below.

TABLE 2

Compounds of the formula:

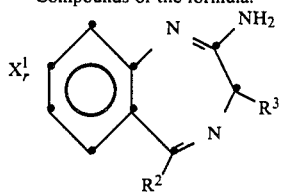

| $X^1$ | r | $R^2$ | $R^3$ |
|---|---|---|---|
| H | 1 | o-F—Ph | —$CH_2$—2-indolyl |
| H | 1 | o-F—Ph | —$CH_2$—3-indolyl |
| H | 1 | o-F—Ph— | $NH(CH_2)_{1-3}$—3-indolyl |
| H | 1 | o-F—Ph | —$NHCH_2$—($CH_2)_2$—3-indolyl, COOEt |
| H | 1 | o-F—Ph | —$CH_2NH(CH_2)_2$—3-indolyl |
| H | 1 | o-F—Ph | —NHCO—$(CH_2)_{0-2}$—2-indolyl |
| H | 1 | o-F—Ph | —NHCO$(CH_2)_{0-2}$—3-indolyl |
| H | 1 | o-F—Ph | NHCO—p-halo-phenyl |
| H | 1 | o-F—Ph | NHCO—m-halo-phenyl |
| H | 1 | o-F—Ph | NHCO—2-benzofuranyl |
| H | 1 | o-F—Ph | 2-(3-methylindenyl) |
| H | 1 | o-F—Ph | phenylethenyl |
| H | 1 | o-F—Ph | NHCONH—p-halophenyl |
| H | 1 | p-Cl—Ph | —$CH_2$—2-indolyl |
| H | 1 | p-Cl—Ph | —$CH_2$—3-indolyl |
| H | 1 | p-Cl—Ph | —$NH(CH_2)_{1-3}$—3-indolyl |
| H | 1 | p-Cl—Ph | —NHCO—$(CH_2)_{0-2}$—2-indolyl |
| H | 1 | p-Cl—Ph | NHCO—p-halo-phenyl |
| H | 1 | p-Cl—Ph | NHCO—m-halo-phenyl |
| H | 1 | p-Cl—Ph | NHCO—2-benzofuranyl |
| H | 1 | p-Cl—Ph | 2—(3-methylindenyl) |
| H | 1 | p-Cl—Ph | phenylethenyl |
| H | 1 | p-Cl—Ph | NHCONH—p-halo-phenyl |
| H | 1 | phenyl | —$CH_2$—2-indolyl |
| H | 1 | phenyl | —$CH_2$—3-indolyl |
| H | 1 | phenyl | —NHCO$(CH_2)_{0-2}$—indolyl |
| H | 1 | phenyl | —$NH(CH_2)_{1-3}$—3-indolyl |
| H | 1 | phenyl | NHCO—p-halo-phenyl |
| H | 1 | phenyl | NHCO—m-halo-phenyl |
| H | 1 | phenyl | NHCO—2-benzofuranyl |
| H | 1 | phenyl | 2-(3-methylindenyl) |
| H | 1 | phenyl | phenylethenyl |
| H | 1 | phenyl | NHCONH—p-halo-phenyl |
| H | 1 | p-F—Ph | —$CH_2$—2-indolyl |
| H | 1 | p-F—Ph | —$CH_2$—3-indolyl |
| H | 1 | p-F—Ph | —NHCO$(CH_2)_{0-2}$—2-indolyl |
| H | 1 | p-F—Ph | —$NH(CH_2)_{1-3}$—3-indolyl |
| H | 1 | p-F—Ph | NHCO—p-halo-phenyl |
| H | 1 | p-F—Ph | NHCO—m-halo-phenyl |
| H | 1 | p-F—Ph | NHCO—2-benzofuranyl |
| H | 1 | p-F—Ph | 2-(3-methylindenyl) |
| H | 1 | p-F—Ph | phenylethenyl |
| H | 1 | p-F—Ph | NHCONH—p-halophenyl |
| H | 1 | 2,4-di-Cl—Ph | —$CH_2$—2-indolyl |
| H | 1 | 2,4-di-Cl—Ph | —$CH_2$—3-indolyl |
| H | 1 | 2,4-di-Cl—Ph | —NHCO$(CH_2)_{0-2}$—2-indolyl |
| H | 1 | 2,4-di-Cl—Ph | —$NH(CH_2)_{1-3}$—3-indolyl |
| H | 1 | 2,4-di-Cl—Ph | NHCO—p-halo-phenyl |
| H | 1 | 2,4-di-Cl—Ph | NHCO—m-halo-phenyl |
| H | 1 | 2,4-di-Cl—Ph | NHCO—2-benzofuranyl |
| H | 1 | 2,4-di-Cl—Ph | 2-(3-methylindenyl) |
| H | 1 | 2,4-di-Cl—Ph | phenylethenyl |
| H | 1 | 2,4-di-Cl—Ph | NHCONH—p-halophenyl |
| H | 1 | 2,6-di-F—Ph | —$CH_2$—2-indolyl |
| H | 1 | 2,6-di-F—Ph | —$CH_2$—3-indolyl |
| H | 1 | 2,6-di-F—Ph | —NHCO$(CH_2)_{0-2}$—2-indolyl |
| H | 1 | 2,6-di-F—Ph | —$NH(CH_2)_{1-3}$—3-indolyl |
| H | 1 | 2,6-di-F—Ph | NHCO—p-halo-phenyl |
| H | 1 | 2,6-di-F—Ph | NHCO—m-halo-phenyl |
| H | 1 | 2,6-di-F—Ph | NHCO—2-benzofuranyl |
| H | 1 | 2,6-di-F—Ph | 2-(3-methylindenyl) |
| H | 1 | 2,6-di-F—Ph | phenylethenyl |
| H | 1 | 2,6-di-F—Ph | NHCONH—p-halo-phenyl |
| H | 1 | $CH_2COO$—t-butyl | —$CH_2$—2-indolyl |
| H | 1 | $CH_2COO$—t-butyl | —$CH_2$—3-indolyl |
| H | 1 | $CH_2COO$—t-butyl | —NHCO$(CH_2)_{0-2}$—indolyl |
| H | 1 | $CH_2COO$—t-butyl | —$NH(CH_2)_{1-3}$—3-indolyl |
| H | 1 | $CH_2COO$—t-butyl | NHCO—p-halo-phenyl |
| H | 1 | $CH_2COO$—t-butyl | NHCO—m-halo-phenyl |
| H | 1 | $CH_2COO$—t-butyl | NHCO—2-benzofuranyl |
| H | 1 | $CH_2COO$—t-butyl | 2-(3-methylindenyl) |
| H | 1 | $CH_2COO$—t-butyl | phenylethenyl |
| H | 1 | $CH_2COO$—t-butyl | NHCONH—p-halophenyl |
| H | 1 | —$CH_2COOEt$ | —$CH_2$—2-indolyl |
| H | 1 | —$CH_2COOEt$ | —$CH_2$—3-indolyl |
| H | 1 | —$CH_2COOEt$ | —NHCO$(CH_2)_{0-2}$—indolyl |
| H | 1 | —$CH_2COOEt$ | —$NH(CH_2)_{1-3}$—3-indolyl |
| H | 1 | —$CH_2COOEt$ | NHCO—p-halo-phenyl |
| H | 1 | —$CH_2COOEt$ | NHCO—m-halo-phenyl |
| H | 1 | —$CH_2COOEt$ | NHCO—2-benzofuranyl |
| H | 1 | —$CH_2COOEt$ | 2-(3-methylindenyl) |
| H | 1 | —$CH_2COOEt$ | phenylethenyl |
| H | 1 | —$CH_2COOEt$ | NHDONH—p-halophenyl |
| Cl | 1 | p-Cl—Ph | —$CH_2$—2-indolyl |
| Cl | 1 | p-Cl—Ph | —$CH_2$—3-indolyl |
| Cl | 1 | p-Cl—Ph | —NHCO$(CH_2)_{0-2}$—2-indolyl |
| Cl | 1 | p-Cl—Ph | —$NH(CH_2)_{1-3}$—3-indolyl |
| Cl | 1 | p-Cl—Ph | NHCO—p-halo-phenyl |
| Cl | 1 | p-Cl—Ph | NHCO—m-halo-phenyl |
| Cl | 1 | p-Cl—Ph | NHCO—2-benzofuranyl |
| Cl | 1 | p-Cl—Ph | 2-(3-metnylindenyl) |
| Cl | 1 | p-Cl—Ph | phenylethenyl |
| Cl | 1 | p-Cl—Ph | NHCONH—p-halophenyl |
| Cl | 1 | Ph | —$CH_2$—2-indolyl |
| Cl | 1 | Ph | —$CH_2$—3-indolyl |
| Cl | 1 | Ph | —NHCO$(CH_2)_{0-2}$—2-indolyl |
| Cl | 1 | Ph | —$NH(CH_2)_{1-3}$—3-indolyl |
| Cl | 1 | Ph | NHCO—p-halo-phenyl |
| Cl | 1 | Ph | NHCO—m-halo-phenyl |
| Cl | 1 | Ph | NHCO—2-benzofuranyl |
| Cl | 1 | Ph | 2-(3-methylindenyl) |
| Cl | 1 | Ph | phenylethenyl |
| Cl | 1 | Ph | NHCONH—p-halophenyl |
| Cl | 1 | p-F—Ph | —$CH_2$—2-indolyl |
| Cl | 1 | p-F—Ph | —$CH_2$—3-indolyl |
| Cl | 1 | p-F—Ph | —NHCO$(CH_2)_{0-2}$—2-indolyl |
| Cl | 1 | p-F—Ph | —$NH(CH_2)_{1-3}$—3-indolyl |
| Cl | 1 | p-F—Ph | NHCO—p-halo-phenyl |
| Cl | 1 | p-F—Ph | NHCO—m-halo-phenyl |
| Cl | 1 | p-F—Ph | NHCO—2-benzofuranyl |
| Cl | 1 | p-F—Ph | 2-(3-methylindenyl) |
| Cl | 1 | p-F—Ph | phenylethenyl |
| Cl | 1 | p-F—Ph | NHCONH—p-halophenyl |
| Cl | 1 | p-F—Ph | —$CH_2$—2-indolyl |
| Cl | 1 | p-F—Ph | —$CH_2$—3-indolyl |
| Cl | 1 | p-F—Ph | —NHCO$(CH_2)_{0-2}$—2-indolyl |
| Cl | 1 | p-F—Ph | —$NH(CH_2)_{1-3}$—3-indolyl |
| Cl | 1 | p-F—Ph | NHCO—p-halo-phenyl |
| Cl | 1 | p-F—Ph | NHCO—m-halo-phenyl |
| Cl | 1 | p-F—Ph | NHCO—2-benzofuranyl |
| Cl | 1 | p-F—Ph | 2-(3-methylindenyl) |

TABLE 2-continued

Compounds of the formula:

| $X^1$ | r | $R^2$ | $R^3$ |
|---|---|---|---|
| Cl | 1 | p-F—Ph | phenylethenyl |
| Cl | 1 | p-F—Ph | NHCONH—p-halophenyl |
| F | 1 | 2,4-di-Cl—Ph | —CH$_2$—2-indolyl |
| F | 1 | 2,6-di-Cl—Ph | —CH$_2$—3-indolyl |
| F | 1 | 2,6-di-Cl—Ph | —NHCO(CH$_2$)$_{0-2}$—2-indolyl |
| F | 1 | 2,6-di-Cl—Ph | —NH(CH$_2$)$_{1-3}$—3-indolyl |
| F | 1 | 2,6-di-Cl—Ph | NHCO—p-halo-phenyl |
| F | 1 | 2,6-di-Cl—Ph | NHCO—m-halo-phenyl |
| F | 1 | 2,6-di-Cl—Ph | NHCO—2-benzofuranyl |
| F | 1 | 2,6-di-Cl—Ph | 2-(3-methylindenyl) |
| F | 1 | 2,6-di-Cl—Ph | phenylethenyl |
| F | 1 | 2,6-di-Cl—Ph | NHCONH—p-halophenyl |
| F | 1 | 2,6-di-F—Ph | —CH$_2$—2-indolyl |
| F | 1 | 2,6-di-F—Ph | —CH$_2$—3-indolyl |
| F | 1 | 2,6-di-F—Ph | —NHCO(CH$_2$)$_{0-2}$—2-indolyl |
| F | 1 | 2,6-di-F—Ph | —NH(CH$_2$)$_{1-3}$—3-indolyl |
| F | 1 | 2,6-di-F—Ph | NHCO—p-halo-phenyl |
| F | 1 | 2,6-di-F—Ph | NHCO—m-halo-phenyl |
| F | 1 | 2,6-di-F—Ph | NHCO—2-benzofuranyl |
| F | 1 | 2,6-di-F—Ph | 2-(3-methylindenyl) |
| F | 1 | 2,6-di-F—Ph | phenylethenyl |
| F | 1 | 2,6-di-F—Ph | NHCONH—p-halo-phenyl |
| F | 1 | COO—t-butyl | —CH$_2$—2-indolyl |
| F | 1 | COO—t-butyl | —CH$_2$—3-indolyl |
| F | 1 | COO—t-butyl | —NHCO(CH$_2$)$_{0-2}$—2-indolyl |
| F | 1 | COO—t-butyl | —NH(CH$_2$)$_{1-3}$—3-indolyl |
| F | 1 | COO—t-butyl | NHCO—p-halo-phenyl |
| F | 1 | COO—t-butyl | NHCO—m-halo-phenyl |
| F | 1 | COO—t-butyl | NHCO—2-benzofuranyl |
| F | 1 | COO—t-butyl | 2-(3-methylindenyl) |
| F | 1 | COO—t-butyl | phenylethenyl |
| F | 1 | COO—t-butyl | NHCONH—p-halo-phenyl |
| F | 1 | —CH$_2$COOEt | —CH$_2$—2-indolyl |
| F | 1 | —CH$_2$COOEt | —CH$_2$—3-indolyl |
| F | 1 | —CH$_2$COOEt | —NHCO(CH$_2$)$_{0-2}$—2-indolyl |
| F | 1 | —CH$_2$COOEt | —NH(CH$_2$)$_{1-3}$—3-indolyl |
| F | 1 | —CH$_2$COOEt | NHCO—p-halo-phenyl |
| F | 1 | —CH$_2$COOEt | NHCO—m-halo-phenyl |
| F | 1 | —CH$_2$COOEt | NHCO—2-benzofuranyl |
| F | 1 | —CH$_2$COOEt | 2-(3-methylindenyl) |
| F | 1 | —CH$_2$COOEt | phenylethenyl |
| F | 1 | —CH$_2$COOEt | NHCONH—p-halo-phenyl |
| CF$_3$ | 1 | p-Cl—Ph | —CH$_2$—2-indolyl |
| CF$_3$ | 1 | p-Cl—Ph | —CH$_2$—3-indolyl |
| CF$_3$ | 1 | p-Cl—Ph | —NHCO(CH$_2$)$_{0-2}$—2-indolyl |
| CF$_3$ | 1 | p-Cl—Ph | —NH(CH$_2$)$_{1-3}$—3-indolyl |
| CF$_3$ | 1 | p-Cl—Ph | NHCO—p-halo-phenyl |
| CF$_3$ | 1 | p-Cl—Ph | NHCO—m-halo-phenyl |
| CF$_3$ | 1 | p-Cl—Ph | NHCO—2-benzofuranyl |
| CF$_3$ | 1 | p-Cl—Ph | 2-(3-methylindenyl) |
| CF$_3$ | 1 | p-Cl—Ph | phenylethenyl |
| CF$_3$ | 1 | p-Cl—Ph | NHCONH—p-halo-phenyl |
| CF$_3$ | 1 | Ph | —CH$_2$—2-indolyl |
| CF$_3$ | 1 | Ph | —CH$_2$—3-indolyl |
| CF$_3$ | 1 | Ph | —NHCO(CH$_2$)$_{0-2}$—2-indolyl |
| CF$_3$ | 1 | Ph | —NH(CH$_2$)$_{1-3}$—3-indolyl |
| CF$_3$ | 1 | Ph | NHCO—p-halo-phenyl |
| CF$_3$ | 1 | Ph | NHCO—m-halo-phenyl |
| CF$_3$ | 1 | Ph | NHCO—2-benzofuranyl |
| CF$_3$ | 1 | Ph | 2-(3-methylindenyl) |
| CF$_3$ | 1 | Ph | phenylethenyl |
| CF$_3$ | 1 | Ph | NHCONH—p-halo-phenyl |
| CF$_3$ | 1 | p-F—Ph | —CH$_2$—2-indolyl |
| CF$_3$ | 1 | p-F—Ph | —CH$_2$—3-indolyl |
| CF$_3$ | 1 | p-F—Ph | —NHCO(CH$_2$)$_{0-2}$—2-indolyl |
| CF$_3$ | 1 | p-F—Ph | —NH(CH$_2$)$_{1-3}$—3-indolyl |
| CF$_3$ | 1 | p-F—Ph | NHCO—p-halo-phenyl |
| CF$_3$ | 1 | p-F—Ph | NHCO—m-halo-phenyl |
| CF$_3$ | 1 | p-F—Ph | NHCO—2-benzofuranyl |
| CF$_3$ | 1 | p-F—Ph | 2-(3-methylindenyl) |
| CF$_3$ | 1 | p-F—Ph | phenylethenyl |
| CF$_3$ | 1 | p-F—Ph | NHCONH—p-halo-phenyl |
| CF$_3$ | 1 | p-F—Ph | —CH$_2$—2-indolyl |
| CF$_3$ | 1 | p-F—Ph | —CH$_2$—3-indolyl |
| CF$_3$ | 1 | p-F—Ph | —NHCO(CH$_2$)$_{0-2}$—2-indolyl |
| CF$_3$ | 1 | p-F—Ph | —NH(CH$_2$)$_{1-3}$—3-indolyl |
| CF$_3$ | 1 | p-F—Ph | NHCO—p-halo-phenyl |
| CF$_3$ | 1 | p-F—Ph | NHCO—m-halo-phenyl |
| CF$_3$ | 1 | p-F—Ph | NHCO—2-benzofuranyl |
| CF$_3$ | 1 | p-F—Ph | 2-(3-methylindenyl) |
| CF$_3$ | 1 | p-F—Ph | phenylethenyl |
| CF$_3$ | 1 | p-F—Ph | NHCONH—p-halo-phenyl |
| NO$_2$ | 1 | Ph | —CH$_2$—2-indolyl |
| NO$_2$ | 1 | p-Cl—Ph | —CH$_2$—3-indolyl |
| NO$_2$ | 1 | Ph | —NHCO(CH$_2$)$_{0-2}$—2-indolyl |
| NO$_2$ | 1 | Ph | —NH(CH$_2$)$_{1-3}$—3-indolyl |
| NO$_2$ | 1 | Ph | NHCO—p-halo-phenyl |
| NO$_2$ | 1 | Ph | NHCO—m-halo-phenyl |
| NO$_2$ | 1 | Ph | NHCO—2-benzofuranyl |
| NO$_2$ | 1 | Ph | 2-(3-methylindenyl) |
| NO$_2$ | 1 | Ph | phenylethenyl |
| NO$_2$ | 1 | Ph | NHCONH—p-halo-phenyl |
| NO$_2$ | 1 | Ph | —CH$_2$—2-indolyl |
| NO$_2$ | 1 | Ph | —CH$_2$—3-indolyl |
| NO$_2$ | 1 | Ph | —NHCO(CH$_2$)$_{0-2}$—2-indolyl |
| NO$_2$ | 1 | Ph | —NH(CH$_2$)$_{1-3}$—3-indolyl |
| NO$_2$ | 1 | Ph | NHCO—p-halo-phenyl |
| NO$_2$ | 1 | Ph | NHCO—m-halo-phenyl |
| NO$_2$ | 1 | Ph | NHCO—2-benzofuranyl |
| NO$_2$ | 1 | Ph | 2-(3-methylindenyl) |
| NO$_2$ | 1 | Ph | phenylethenyl |
| NO$_2$ | 1 | Ph | NHCONH—p-halo-phenyl |
| NO$_2$ | 1 | p-F—Ph | —CH$_2$—2-indolyl |
| NO$_2$ | 1 | p-F—Ph | —CH$_2$—3-indolyl |
| NO$_2$ | 1 | p-F—Ph | —NHCO(CH$_2$)$_{0-2}$—2-indolyl |
| NO$_2$ | 1 | p-F—Ph | —NH(CH$_2$)$_{1-3}$—3-indolyl |
| NO$_2$ | 1 | p-F—Ph | NHCO—p-halo-phenyl |
| NO$_2$ | 1 | p-F—Ph | NHCO—m-halo-phenyl |
| NO$_2$ | 1 | p-F—Ph | NHCO—2-benzofuranyl |
| NO$_2$ | 1 | p-F—Ph | 2-(3-methylindenyl) |
| NO$_2$ | 1 | p-F—Ph | phenylethenyl |
| NO$_2$ | 1 | p-F—Ph | NHCONH—p-halo-phenyl |
| NO$_2$ | 1 | p-F—Ph | —CH$_2$—2-indolyl |
| NO$_2$ | 1 | p-F—Ph | —CH$_2$—3-indolyl |
| NO$_2$ | 1 | p-F—Ph | —NHCO(CH$_2$)$_{0-2}$—2-indolyl |
| NO$_2$ | 1 | p-F—Ph | —NH(CH$_2$)$_{1-3}$—3-indolyl |
| NO$_2$ | 1 | p-F—Ph | NHCO—p-halo-phenyl |
| NO$_2$ | 1 | p-F—Ph | NHCO—m-halo-phenyl |
| NO$_2$ | 1 | p-F—Ph | NHCO—2-benzofuranyl |
| NO$_2$ | 1 | p-F—Ph | 2-(3-methylindenyl) |
| NO$_2$ | 1 | p-F—Ph | phenylethenyl |
| NO$_2$ | 1 | p-F—Ph | NHCONH—p-halo-phenyl |
| CH$_3$ | 1 | phenyl | —CH$_2$—2-indolyl |
| CH$_3$ | 1 | phenyl | —CH$_2$—3-indolyl |
| CH$_3$ | 1 | phenyl | —NHCO(CH$_2$)$_{0-2}$—2-indolyl |
| CH$_3$ | 1 | phenyl | —NH(CH$_2$)$_{1-3}$—3-indolyl |
| CH$_3$ | 1 | phenyl | NHCO—p-halo-phenyl |
| CH$_3$ | 1 | phenyl | NHCO—m-halo-phenyl |
| CH$_3$ | 1 | phenyl | NHCO—2-benzofuranyl |
| CH$_3$ | 1 | phenyl | 2-(3-methylindenyl) |
| CH$_3$ | 1 | phenyl | phenylethenyl |
| CH$_3$ | 1 | phenyl | NHCONH—p-halo-phenyl |
| H | 1 | o-F—Ph | —CH$_2$—2-indolyl |
| H | 1 | o-F—Ph | —CH$_2$—3-indolyl |
| H | 1 | o-F—Ph | —NHCO(CH$_2$)$_{0-2}$—2-indolyl |
| H | 1 | o-F—Ph | —NH(CH$_2$)$_{1-3}$—3-indolyl |
| H | 1 | o-F—Ph | NHCO—p-halo-phenyl |
| H | 1 | o-F—Ph | NHCO—m-halo-phenyl |
| H | 1 | o-F—Ph | NHCO—2-benzofuranyl |
| H | 1 | o-F—Ph | 2-(3-methylindenyl) |

TABLE 2-continued

Compounds of the formula:

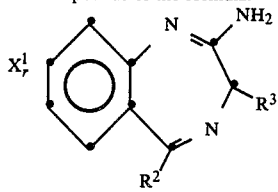

| X¹ | r | R² | R³ |
|---|---|---|---|
| H | 1 | o-F—Ph | phenylethenyl |
| H | 1 | o-F—Ph | NHCONH—p-halo-phenyl |
| H | 1 | p-Cl—Ph | —CH₂—2-indolyl |
| H | 1 | p-Cl—Ph | —CH₂—3-indolyl |
| H | 1 | p-Cl—Ph | —NHCO(CH₂)₀₋₂—2-indolyl |
| H | 1 | p-Cl—Ph | —NH(CH₂)₁₋₃—3-indolyl |
| H | 1 | p-Cl—Ph | NHCO—p-halo-phenyl |
| H | 1 | p-Cl—Ph | NHCO—m-halo-phenyl |
| H | 1 | p-Cl—Ph | NHCO—2-benzofuranyl |
| H | 1 | p-Cl—Ph | 2-(3-methylindenyl) |
| H | 1 | p-Cl—Ph | phenylethenyl |
| H | 1 | p-Cl—Ph | NHCONH—p-halo-phenyl |
| H | 1 | o-F—Ph | CH₂—2 or 3-(1-methylindolyl) |
| H | 1 | —CH₂COO—t-butyl | CH₂—2 or 3-(1-methylindolyl) |
| H | 1 | —CH₂COOEt | CH₂—2 or 3-(1-methylindolyl) |
| H | 1 | Ph | CH₂—2 or 3-(1-methylindolyl) |
| H | 1 | —CH₂COO—t-butyl | NHCO(CH₂)₀₋₂—2-indolyl |
| H | 1 | —CH₂COOEt | NHCO(CH₂)₀₋₂—2-indolyl |
| H | 1 | Ph | NHCO(CH₂)₀₋₂—2-indolyl |
| H | 1 | o-F—Ph | NHCO(CH₂)₀₋₂—2 or 3-(1-methylindolyl) |
| H | 1 | —CH₂COO—t-butyl | NHCO(CH₂)₀₋₂—2 or 3-(1-methylindolyl) |
| H | 1 | —CH₂COOEt | NHCO(CH₂)₀₋₂—2 or 3-(1-methylindolyl) |
| H | 1 | Ph | NHCO(CH₂)₀₋₂—2 or 3-(1-methylindolyl) |
| H | 1 | o-F—Ph | NH(CH₂)₁₋₃—2-indolyl |
| H | 1 | —CH₂COO—t-butyl | NH(CH₂)₁₋₃—2-indolyl |
| H | 1 | —CH₂COOEt | NH(CH₂)₁₋₃—2-indolyl |
| H | 1 | Ph | NH(CH₂)₁₋₃—2-indolyl |
| H | 1 | o-F—Ph | NH(CH₂)₁₋₃—2 or 3-(1-methylindolyl) |
| H | 1 | —CH₂COO—t-butyl | NH(CH₂)₁₋₃—2 or 3-(1-methylindolyl) |
| H | 1 | —CH₂COOEt | NH(CH₂)₁₋₃—2 or 3-(1-methylindolyl) |
| H | 1 | Ph | NH(CH₂)₁₋₃—2 or 3-(1-methylindolyl) |
| H | 1 | o-F—Ph | NHCH(CH₂)₂—2-indolyl<br>\|<br>COOEt |
| H | 1 | —CH₂COO—t-butyl | NHCH(CH₂)₂—2-indolyl<br>\|<br>COOEt |
| H | 1 | —CH₂COOEt | NHCH(CH₂)₂—2-indolyl<br>\|<br>COOEt |
| H | 1 | Ph | NHCH(CH₂)₂—2-indolyl<br>\|<br>COOEt |
| H | 1 | o-F—Ph | COOEt<br>\|<br>NHCH(CH₂)₂—2 or 3-(1-methylindolyl) |
| H | 1 | —CH₂COO—t-butyl | COOEt<br>\|<br>NHCH(CH₂)₂—2 or 3-(1-methylindolyl) |
| H | 1 | —CH₂COOEt | COOEt<br>\|<br>NHCH(CH₂)₂—2 or 3-(1-methylindolyl) |

TABLE 2-continued

Compounds of the formula:

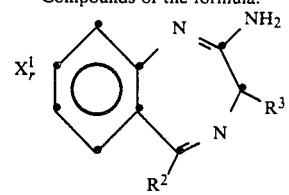

| X¹ | r | R² | R³ |
|---|---|---|---|
| H | 1 | Ph | COOEt<br>\|<br>NHCH(CH₂)₂—2 or 3-(1-methylindolyl) |
| H | 1 | o-F—Ph | NHCH(CH₂)₂—2 or 3-indolyl-<br>\|<br>COO—t-Butyl |
| H | 1 | —CH₂COO—t-butyl | NHCH(CH₂)₂—2 or 3-indolyl-<br>\|<br>COO—t-Butyl |
| H | 1 | —CH₂COOEt | NHCH(CH₂)₂—2 or 3-indolyl-<br>\|<br>COO—t-Butyl |
| H | 1 | Ph | NHCH(CH₂)₂—2 or 3-indolyl-<br>\|<br>COO—t-Butyl |
| H | 1 | o-F—Ph | COO—t-Butyl<br>\|<br>NHCH(CH₂)₂—2 or 3-(1-methylindolyl) |
| H | 1 | —CH₂COO—t-butyl | COO—t-Butyl<br>\|<br>NHCH(CH₂)₂—2 or 3-(1-methylindolyl) |
| H | 1 | —CH₂COOEt | COO—t-Butyl<br>\|<br>NHCH(CH₂)₂—2 or 3-(1-methylindolyl) |
| H | 1 | Ph | COO—t-Butyl<br>\|<br>NHCH(CH₂)₂—2 or 3-(1-methylindolyl) |

TABLE 3

Compounds of the formula:

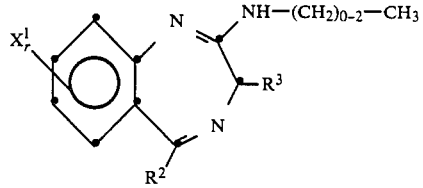

| X¹ | r | R² | R³ |
|---|---|---|---|
| H | 1 | o-F—Ph | —CH₂—2-indolyl |
| H | 1 | o-F—Ph | —CH₂—3-indolyl |
| H | 1 | o-F—Ph— | NH(CH₂)₁₋₃—3-indolyl |
| H | 1 | o-F—Ph | —NHCH₂—(CH₂)₂—3-indolyl<br>\|<br>COOEt |
| H | 1 | o-F—Ph | —CH₂NH(CH₂)₂—3-indolyl |
| H | 1 | o-F—Ph | —NHCO—(CH₂)₀₋₂—2-indolyl |
| H | 1 | o-F—Ph | —NHCO(CH₂)₀₋₂—3-indolyl |

TABLE 3-continued

Compounds of the formula:

$$X^1_r \text{—Ph—C(=N-(CH}_2)_{0-2}\text{-CH}_3)\text{-CH(R}^3)\text{-N=C(R}^2)$$

| $X^1$ | r | $R^2$ | $R^3$ |
|---|---|---|---|
| H | 1 | o-F—Ph | NHCO—p-halo-phenyl |
| H | 1 | o-F—Ph | NHCO—m-halo-phenyl |
| H | 1 | o-F—Ph | NHCO—2-benzofuranyl |
| H | 1 | o-F—Ph | 2-(3-methylindenyl) |
| H | 1 | o-F—Ph | phenylethenyl |
| H | 1 | o-F—Ph | NHCONH—p-halo-phenyl |
| H | 1 | p-Cl—Ph | —CH$_2$—2-indolyl |
| H | 1 | p-Cl—Ph | —CH$_2$—3-indolyl |
| H | 1 | p-Cl—Ph | —NH(CH$_2$)$_{1-3}$—3-indolyl |
| H | 1 | p-Cl—Ph | —NHCO—(CH$_2$)$_{0-2}$—2-indolyl |
| H | 1 | p-Cl—Ph | NHCO—p-halo-phenyl |
| H | 1 | p-Cl—Ph | NHCO—m-halo-phenyl |
| H | 1 | p-Cl—Ph | NHCO—2-benzofuranyl |
| H | 1 | p-Cl—Ph | 2-(3-methylindenyl) |
| H | 1 | p-Cl—Ph | phenylethenyl |
| H | 1 | p-Cl—Ph | NHCONH—p-halo-phenyl |
| H | 1 | phenyl | —CH$_2$—2-indolyl |
| H | 1 | phenyl | —CH$_2$—3-indolyl |
| H | 1 | phenyl | —NHCO(CH$_2$)$_{0-2}$-indolyl |
| H | 1 | phenyl | —NH(CH$_2$)$_{1-3}$—3-indolyl |
| H | 1 | phenyl | NHCO—p-halo-phenyl |
| H | 1 | phenyl | NHCO—m-halo-phenyl |
| H | 1 | phenyl | NHCO—2-benzofuranyl |
| H | 1 | phenyl | 2-(3-methylindenyl) |
| H | 1 | phenyl | phenylethenyl |
| H | 1 | phenyl | NHCONH—p-halo-phenyl |
| H | 1 | p-F—Ph | —CH$_2$—2-indolyl |
| H | 1 | p-F—Ph | —CH$_2$—3-indolyl |
| H | 1 | p-F—Ph | —NHCO(CH$_2$)$_{0-2}$—2-indolyl |
| H | 1 | p-F—Ph | —NH(CH$_2$)$_{1-3}$—3-indolyl |
| H | 1 | p-F—Ph | NHCO—p-halo-phenyl |
| H | 1 | p-F—Ph | NHCO—m-halo-phenyl |
| H | 1 | p-F—Ph | NHCO—2-benzofuranyl |
| H | 1 | p-F—Ph | 2-(3-methylindenyl) |
| H | 1 | p-F—Ph | phenylethenyl |
| H | 1 | p-F—Ph | NHCONH—p-halo-phenyl |
| H | 1 | 2,4-di-Cl—Ph | —CH$_2$—2-indolyl |
| H | 1 | 2,4-di-Cl—Ph | —CH$_2$—3-indolyl |
| H | 1 | 2,4-di-Cl—Ph | —NHCO(CH$_2$)$_{0-2}$—2-indolyl |
| H | 1 | 2,4-di-Cl—Ph | —NH(CH$_2$)$_{1-3}$—3-indolyl |
| H | 1 | 2,4-di-Cl—Ph | NHCO—p-halo-phenyl |
| H | 1 | 2,4-di-Cl—Ph | NHCO—m-halo-phenyl |
| H | 1 | 2,4-di-Cl—Ph | NHCO—2-benzofuranyl |
| H | 1 | 2,4-di-Cl—Ph | 2-(3-methylindenyl) |
| H | 1 | 2,4-di-Cl—Ph | phenylethenyl |
| H | 1 | 2,4-di-Cl—Ph | NHCONH—p-halo-phenyl |
| H | 1 | 2,6-di-F—Ph | —CH$_2$—2-indolyl |
| H | 1 | 2,6-di-F—Ph | —CH$_2$—3-indolyl |
| H | 1 | 2,6-di-F—Ph | —NHCO(CH$_2$)$_{0-2}$—2-indolyl |
| H | 1 | 2,6-di-F—Ph | —NH(CH$_2$)$_{1-3}$—3-indolyl |
| H | 1 | 2,6-di-F—Ph | NHCO—p-halo-phenyl |
| H | 1 | 2,6-di-F—Ph | NHCO—m-halo-phenyl |
| H | 1 | 2,6-di-F—Ph | NHCO—2-benzofuranyl |
| H | 1 | 2,6-di-F—Ph | 2-(3-methylindenyl) |
| H | 1 | 2,6-di-F—Ph | phenylethenyl |
| H | 1 | 2,6-di-F—Ph | NHCONH—p-halo-phenyl |
| H | 1 | CH$_2$COO—t-butyl | —CH$_2$—2-indolyl |
| H | 1 | CH$_2$COO—t-butyl | —CH$_2$—3-indolyl |
| H | 1 | CH$_2$COO—t-butyl | —NHCO(CH$_2$)$_{0-2}$—indolyl |
| H | 1 | CH$_2$COO—t-butyl | —NH(CH$_2$)$_{1-3}$—3-indolyl |
| H | 1 | CH$_2$COO—t-butyl | NHCO—p-halo-phenyl |
| H | 1 | CH$_2$COO—t-butyl | NHCO—m-halo-phenyl |
| H | 1 | CH$_2$COO—t-butyl | NHCO—2-benzofuranyl |
| H | 1 | CH$_2$COO—t-butyl | 2-(3-methylindenyl) |
| H | 1 | CH$_2$COO—t-butyl | phenylethenyl |
| H | 1 | CH$_2$COO—t-butyl | NHCONH—p-halo-phenyl |
| H | 1 | —CH$_2$COOEt | —CH$_2$—2-indolyl |
| H | 1 | —CH$_2$COOEt | —CH$_2$—3-indolyl |
| H | 1 | —CH$_2$COOEt | —NHCO(CH$_2$)$_{0-2}$—indolyl |
| H | 1 | —CH$_2$COOEt | —NH(CH$_2$)$_{1-3}$—3-indolyl |
| H | 1 | —CH$_2$COOEt | NHCO—p-halo-phenyl |
| H | 1 | —CH$_2$COOEt | NHCO—m-halo-phenyl |
| H | 1 | —CH$_2$COOEt | NHCO—2-benzofuranyl |
| H | 1 | —CH$_2$COOEt | 2-(3-methylindenyl) |
| H | 1 | —CH$_2$COOEt | phenylethenyl |
| H | 1 | —CH$_2$COOEt | NHCONH—p-halo-phenyl |
| Cl | 1 | p-Cl—Ph | —CH$_2$—2-indolyl |
| Cl | 1 | p-Cl—Ph | —CH$_2$—3-indolyl |
| Cl | 1 | p-Cl—Ph | —NHCO(CH$_2$)$_{0-2}$—2-indolyl |
| Cl | 1 | p-Cl—Ph | —NH(CH$_2$)$_{1-3}$—3-indolyl |
| Cl | 1 | p-Cl—Ph | NHCO—p-halo-phenyl |
| Cl | 1 | p-Cl—Ph | NHCO—m-halo-phenyl |
| Cl | 1 | p-Cl—Ph | NHCO—2-benzofuranyl |
| Cl | 1 | p-Cl—Ph | 2-(3-methylindenyl) |
| Cl | 1 | p-Cl—Ph | phenylethenyl |
| Cl | 1 | p-Cl—Ph | NHCONH—p-halo-phenyl |
| Cl | 1 | Ph | —CH$_2$—2-indolyl |
| Cl | 1 | Ph | —CH$_2$—3-indolyl |
| Cl | 1 | Ph | —NHCO(CH$_2$)$_{0-2}$—2-indolyl |
| Cl | 1 | Ph | —NH(CH$_2$)$_{1-3}$—3-indolyl |
| Cl | 1 | Ph | NHCO—p-halo-phenyl |
| Cl | 1 | Ph | NHCO—m-halo-phenyl |
| Cl | 1 | Ph | NHCO—2-benzofuranyl |
| Cl | 1 | Ph | 2-(3-methylindenyl) |
| Cl | 1 | Ph | phenylethenyl |
| Cl | 1 | Ph | NHCONH—p-halo-phenyl |
| Cl | 1 | o-F—Ph | —CH$_2$—2-indolyl |
| Cl | 1 | o-F—Ph | —CH$_2$—3-indolyl |
| Cl | 1 | o-F—Ph | —NHCO(CH$_2$)$_{0-2}$—2-indolyl |
| Cl | 1 | o-F—Ph | —NH(CH$_2$)$_{1-3}$—3-indolyl |
| Cl | 1 | o-F—Ph | NHCO—p-halo-phenyl |
| Cl | 1 | o-F—Ph | NHCO—m-halo-phenyl |
| Cl | 1 | o-F—Ph | NHCO—2-benzofuranyl |
| Cl | 1 | o-F—Ph | 2-(3-methylindenyl) |
| Cl | 1 | o-F—Ph | phenylethenyl |
| Cl | 1 | o-F—Ph | NHCONH—p-halo-phenyl |
| Cl | 1 | p-F—Ph | —CH$_2$—2-indolyl |
| Cl | 1 | p-F—Ph | —CH$_2$—3-indolyl |
| Cl | 1 | p-F—Ph | —NHCO(CH$_2$)$_{0-2}$—2-indolyl |
| Cl | 1 | p-F—Ph | —NH(CH$_2$)$_{1-3}$—3-indolyl |
| Cl | 1 | p-F—Ph | NHCO—p-halo-phenyl |
| Cl | 1 | p-F—Ph | NHCO—m-halo-phenyl |
| Cl | 1 | p-F—Ph | NHCO—2-benzofuranyl |
| Cl | 1 | p-F—Ph | 2-(3-methylindenyl) |
| Cl | 1 | p-F—Ph | phenylethenyl |
| Cl | 1 | p-F—Ph | NHCONH—p-halo-phenyl |
| F | 1 | 2,4-di-Cl—Ph | —CH$_2$—2-indolyl |
| F | 1 | 2,4-di-Cl—Ph | —CH$_2$—3-indolyl |
| F | 1 | 2,4-di-Cl—Ph | —NHCO(CH$_2$)$_{0-2}$—2-indolyl |
| F | 1 | 2,4-di-Cl—Ph | —NH(CH$_2$)$_{1-3}$—3-indolyl |
| F | 1 | 2,4-di-Cl—Ph | NHCO—p-halo-phenyl |
| F | 1 | 2,4-di-Cl—Ph | NHCO—m-halo-phenyl |
| F | 1 | 2,4-di-Cl—Ph | NHCO—2-benzofuranyl |
| F | 1 | 2,4-di-Cl—Ph | 2-(3-methylindenyl) |
| F | 1 | 2,4-di-Cl—Ph | phenylethenyl |
| F | 1 | 2,4-di-Cl—Ph | NHCONH—p-halo-phenyl |
| F | 1 | 2,6-di-F—Ph | —CH$_2$—2-indolyl |
| F | 1 | 2,6-di-F—Ph | —CH$_2$—3-indolyl |
| F | 1 | 2,6-di-F—Ph | —NHCO(CH$_2$)$_{0-2}$—2-indolyl |
| F | 1 | 2,6-di-F—Ph | —NH(CH$_2$)$_{1-3}$—3-indolyl |
| F | 1 | 2,6-di-F—Ph | NHCO—p-halo-phenyl |
| F | 1 | 2,6-di-F—Ph | NHCO—m-halo-phenyl |
| F | 1 | 2,6-di-F—Ph | NHCO—2-benzofuranyl |
| F | 1 | 2,6-di-F—Ph | 2-(3-methylindenyl) |
| F | 1 | 2,6-di-F—Ph | phenylethenyl |
| F | 1 | 2,6-di-F—Ph | NHCONH—p-halo-phenyl |
| F | 1 | COO—t-butyl | —CH$_2$—2-indolyl |
| F | 1 | COO—t-butyl | —CH$_2$—3-indolyl |
| F | 1 | COO—t-butyl | —NHCO(CH$_2$)$_{0-2}$—2-indolyl |
| F | 1 | COO—t-butyl | —NH(CH$_2$)$_{1-3}$—3-indolyl |

TABLE 3-continued

Compounds of the formula:

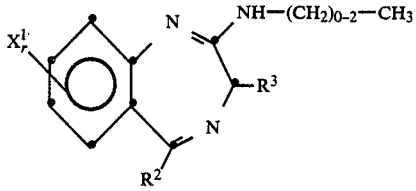
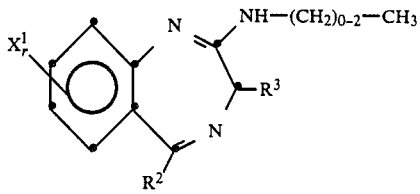

| X¹ | r | R² | R³ |
|---|---|---|---|
| F | 1 | COO—t-butyl | NHCO—p-halo-phenyl |
| F | 1 | COO—t-butyl | NHCO—m-halo-phenyl |
| F | 1 | COO—t-butyl | NHCO—2-benzofuranyl |
| F | 1 | COO—t-butyl | 2-(3-methylindenyl) |
| F | 1 | COO—t-butyl | phenylethenyl |
| F | 1 | COO—t-butyl | NHCONH—p-halo-phenyl |
| F | 1 | —CH₂COOEt | —CH₂—2-indolyl |
| F | 1 | —CH₂COOEt | —CH₂—3-indolyl |
| F | 1 | —CH₂COOEt | —NHCO(CH₂)₀₋₂—2-indolyl |
| F | 1 | —CH₂COOEt | —NH(CH₂)₁₋₃—3-indolyl |
| F | 1 | —CH₂COOEt | NHCO—p-halo-phenyl |
| F | 1 | —CH₂COOEt | NHCO—m-halo-phenyl |
| F | 1 | —CH₂COOEt | NHCO—2-benzofuranyl |
| F | 1 | —CH₂COOEt | 2-(3-methylindenyl) |
| F | 1 | —CH₂COOEt | phenylethenyl |
| F | 1 | —CH₂COOEt | NHCONH—p-halo-phenyl |
| CF₃ | 1 | p-Cl—Ph | —CH₂—2-indolyl |
| CF₃ | 1 | p-Cl—Ph | —CH₂—3-indolyl |
| CF₃ | 1 | p-Cl—Ph | —NHCO(CH₂)₀₋₂—2-indolyl |
| CF₃ | 1 | p-Cl—Ph | —NH(CH₂)₁₋₃—3-indolyl |
| CF₃ | 1 | p-Cl—Ph | NHCO—p-halo-phenyl |
| CF₃ | 1 | p-Cl—Ph | NHCO—m-halo-phenyl |
| CF₃ | 1 | p-Cl—Ph | NHCO—2-benzofuranyl |
| CF₃ | 1 | p-Cl—Ph | 2-(3-methylindenyl) |
| CF₃ | 1 | p-Cl—Ph | phenylethenyl |
| CF₃ | 1 | p-Cl—Ph | NHCONH—p-halo-phenyl |
| CF₃ | 1 | Ph | —CH₂—2-indolyl |
| CF₃ | 1 | Ph | —CH₂—3-indolyl |
| CF₃ | 1 | Ph | —NHCO(CH₂)₀₋₂—2-indolyl |
| CF₃ | 1 | Ph | —NH(CH₂)₁₋₃—3-indolyl |
| CF₃ | 1 | Ph | NHCO—p-halo-phenyl |
| CF₃ | 1 | Ph | NHCO—m-halo-phenyl |
| CF₃ | 1 | Ph | NHCO—2-benzofuranyl |
| CF₃ | 1 | Ph | 2-(3-methylindenyl) |
| CF₃ | 1 | Ph | phenylethenyl |
| CF₃ | 1 | Ph | NHCONH—p-halo-phenyl |
| CF₃ | 1 | o-F—Ph | —CH₂—2-indolyl |
| CF₃ | 1 | o-F—Ph | —CH₂—3-indolyl |
| CF₃ | 1 | o-F—Ph | —NHCO(CH₂)₀₋₂—2-indolyl |
| CF₃ | 1 | o-F—Ph | —NH(CH₂)₁₋₃—3-indolyl |
| CF₃ | 1 | o-F—Ph | NHCO—p-halo-phenyl |
| CF₃ | 1 | o-F—Ph | NHCO—m-halo-phenyl |
| CF₃ | 1 | o-F—Ph | NHCO—2-benzofuranyl |
| CF₃ | 1 | o-F—Ph | 2-(3-methylindenyl) |
| CF₃ | 1 | o-F—Ph | phenylethenyl |
| CF₃ | 1 | o-F—Ph | NHCONH—p-halo-phenyl |
| CF₃ | 1 | p-F—Ph | —CH₂—2-indolyl |
| CF₃ | 1 | p-F—Ph | —CH₂—3-indolyl |
| CF₃ | 1 | p-F—Ph | —NHCO(CH₂)₀₋₂—2-indolyl |
| CF₃ | 1 | p-F—Ph | —NH(CH₂)₁₋₃—3-indolyl |
| CF₃ | 1 | p-F—Ph | NHCO—p-halo-phenyl |
| CF₃ | 1 | p-F—Ph | NHCO—m-halo-phenyl |
| CF₃ | 1 | p-F—Ph | NHCO—2-benzofuranyl |
| CF₃ | 1 | p-F—Ph | 2-(3-methylindenyl) |
| CF₃ | 1 | p-F—Ph | phenylethenyl |
| CF₃ | 1 | p-F—Ph | NHCONH—p-halo-phenyl |
| NO₂ | 1 | p-Cl—Ph | —CH₂—2-indolyl |
| NO₂ | 1 | p-Cl—Ph | —CH₂—3-indolyl |
| NO₂ | 1 | p-Cl—Ph | —NHCO(CH₂)₀₋₂—2-indolyl |
| NO₂ | 1 | p-Cl—Ph | —NH(CH₂)₁₋₃—3-indolyl |
| NO₂ | 1 | p-Cl—Ph | NHCO—p-halo-phenyl |
| NO₂ | 1 | p-Cl—Ph | NHCO—m-halo-phenyl |
| NO₂ | 1 | p-Cl—Ph | NHCO—2-benzofuranyl |
| NO₂ | 1 | p-Cl—Ph | 2-(3-methylindenyl) |
| NO₂ | 1 | p-Cl—Ph | phenylethenyl |
| NO₂ | 1 | p-Cl—Ph | NHCONH—p-halo-phenyl |
| NO₂ | 1 | Ph | —CH₂—2-indolyl |
| NO₂ | 1 | Ph | —CH₂—3-indolyl |
| NO₂ | 1 | Ph | —NHCO(CH₂)₀₋₂—2-indolyl |
| NO₂ | 1 | Ph | —NH(CH₂)₁₋₃—3-indolyl |
| NO₂ | 1 | Ph | NHCO—p-halo-phenyl |
| NO₂ | 1 | Ph | NHCO—m-halo-phenyl |
| NO₂ | 1 | Ph | NHCO—2-benzofuranyl |
| NO₂ | 1 | Ph | 2-(3-methylindenyl) |
| NO₂ | 1 | Ph | phenylethenyl |
| NO₂ | 1 | Ph | NHCONH—p-halo-phenyl |
| NO₂ | 1 | o-F—Ph | —CH₂—2-indolyl |
| NO₂ | 1 | o-F—Ph | —CH₂—3-indolyl |
| NO₂ | 1 | o-F—Ph | —NHCO(CH₂)₀₋₂—2-indolyl |
| NO₂ | 1 | o-F—Ph | —NH(CH₂)₁₋₃—3-indolyl |
| NO₂ | 1 | o-F—Ph | NHCO—p-halo-phenyl |
| NO₂ | 1 | o-F—Ph | NHCO—m-halo-phenyl |
| NO₂ | 1 | o-F—Ph | NHCO—2-benzofuranyl |
| NO₂ | 1 | o-F—Ph | 2-(3-methylindenyl) |
| NO₂ | 1 | o-F—Ph | phenylethenyl |
| NO₂ | 1 | o-F—Ph | NHCONH—p-halo-phenyl |
| NO₂ | 1 | p-F—Ph | —CH₂—2-indolyl |
| NO₂ | 1 | p-F—Ph | —CH₂—3-indolyl |
| NO₂ | 1 | p-F—Ph | —NHCO(CH₂)₀₋₂—2-indolyl |
| NO₂ | 1 | p-F—Ph | —NH(CH₂)₁₋₃—3-indolyl |
| NO₂ | 1 | p-F—Ph | NHCO—p-halo-phenyl |
| NO₂ | 1 | p-F—Ph | NHCO—m-halo-phenyl |
| NO₂ | 1 | p-F—Ph | NHCO—2-benzofuranyl |
| NO₂ | 1 | p-F—Ph | 2-(3-methylindenyl) |
| NO₂ | 1 | p-F—Ph | phenylethenyl |
| NO₂ | 1 | p-F—Ph | NHCONH—p-halo-phenyl |
| CH₃ | 1 | phenyl | —CH₂—2-indolyl |
| CH₃ | 1 | phenyl | —CH₂—3-indolyl |
| CH₃ | 1 | phenyl | —NHCO(CH₂)₀₋₂—2-indolyl |
| CH₃ | 1 | phenyl | —NH(CH₂)₁₋₃—3-indolyl |
| CH₃ | 1 | phenyl | NHCO—p-halo-phenyl |
| CH₃ | 1 | phenyl | NHCO—m-halo-phenyl |
| CH₃ | 1 | phenyl | NHCO—2-benzofuranyl |
| CH₃ | 1 | phenyl | 2-(3-methylindenyl) |
| CH₃ | 1 | phenyl | phenylethenyl |
| CH₃ | 1 | phenyl | NHCONH—p-halo-phenyl |
| H | 1 | o-F—Ph | —CH₂—2-indolyl |
| H | 1 | o-F—Ph | —CH₂—3-indolyl |
| H | 1 | o-F—Ph | —NHCO(CH₂)₀₋₂—2-indolyl |
| H | 1 | o-F—Ph | —NH(CH₂)₁₋₃—3-indolyl |
| H | 1 | o-F—Ph | NHCO—p-halo-phenyl |
| H | 1 | o-F—Ph | NHCO—m-halo-phenyl |
| H | 1 | o-F—Ph | NHCO—2-benzofuranyl |
| H | 1 | o-F—Ph | 2-(3-methylindenyl) |
| H | 1 | o-F—Ph | phenylethenyl |
| H | 1 | o-F—Ph | NHCONH—p-halo-phenyl |
| H | 1 | p-Cl—Ph | —CH₂—2-indolyl |
| H | 1 | p-Cl—Ph | —CH₂—3-indolyl |
| H | 1 | p-Cl—Ph | —NHCO(CH₂)₀₋₂—2-indolyl |
| H | 1 | p-Cl—Ph | —NH(CH₂)₁₋₃—3-indolyl |
| H | 1 | p-Cl—Ph | NHCO—p-halo-phenyl |
| H | 1 | p-Cl—Ph | NHCO—m-halo-phenyl |
| H | 1 | p-Cl—Ph | NHCO—2-benzofuranyl |
| H | 1 | p-Cl—Ph | 2-(3-methylindenyl) |
| H | 1 | p-Cl—Ph | phenylethenyl |
| H | 1 | p-Cl—Ph | NHCONH—p-halo-phenyl |
| H | 1 | o-F—Ph | CH₂—2 or 3-(1-methylindolyl) |
| H | 1 | —CH₂COO—t-butyl | CH₂—2 or 3-(1-methylindolyl) |
| H | 1 | —CH₂COOEt | CH₂—2 or 3-(1-methylindolyl) |
| H | 1 | Ph | CH₂—2 or 3-(1-methylindolyl) |
| H | 1 | o-F—Ph | NHCO(CH₂)₀₋₂—2-indolyl |
| H | 1 | —CH₂COO—t-butyl | NHCO(CH₂)₀₋₂—2-indolyl |
| H | 1 | —CH₂COOEt | NHCO(CH₂)₀₋₂—2-indolyl |
| H | 1 | Ph | NHCO(CH₂)₀₋₂—2-indolyl |
| H | 1 | o-F—Ph | NHCO(CH₂)₀₋₂—2 or 3-(1-methylindolyl) |
| H | 1 | —CH₂COO—t-butyl | NHCO(CH₂)₀₋₂—2 or 3-(1-methylindolyl) |
| H | 1 | —CH₂COOEt | NHCO(CH₂)₀₋₂—2 or 3-(1-methylindolyl) |

TABLE 3-continued

Compounds of the formula:

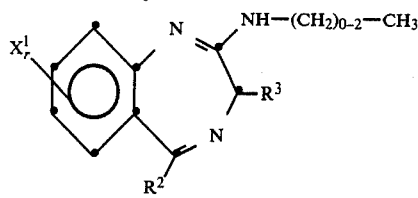

| $X^1$ | r | $R^2$ | $R^3$ |
|---|---|---|---|
| H | 1 | Ph | $NHCO(CH_2)_{0-2}$—2 or 3-(1-methylindolyl) |
| H | 1 | o-F—Ph | $NH(CH_2)_{1-3}$—2-indolyl |
| H | 1 | —$CH_2COO$—t-butyl | $NH(CH_2)_{1-3}$—2-indolyl |
| H | 1 | —$CH_2COOEt$ | $NH(CH_2)_{1-3}$—2-indolyl |
| H | 1 | Ph | $NH(CH_2)_{1-3}$—2-indolyl |
| H | 1 | o-F—Ph | $NH(CH_2)_{1-3}$—2 or 3-(1-methylindolyl) |
| H | 1 | —$CH_2COO$—t-butyl | $NH(CH_2)_{1-3}$—2 or 3-(1-methylindolyl) |
| H | 1 | —$CH_2COOEt$ | $NH(CH_2)_{1-3}$—2 or 3-(1-methylindolyl) |
| H | 1 | Ph | $NH(CH_2)_{1-3}$—2 or 3-(1-methylindolyl) |
| H | 1 | o-F—Ph | $NHCH(CH_2)_2$—2-indolyl<br>\|<br>COOEt |
| H | 1 | —$CH_2COO$—t-butyl | $NHCH(CH_2)_2$—2-indolyl<br>\|<br>COOEt |
| H | 1 | —$CH_2COOEt$ | $NHCH(CH_2)_2$—2-indolyl<br>\|<br>COOEt |
| H | 1 | Ph | $NHCH(CH_2)_2$—2-indolyl<br>\|<br>COOEt |
| H | 1 | o-F—Ph | COOEt<br>\|<br>$NHCH(CH_2)_2$—2 or 3-(1-methylindolyl) |
| H | 1 | —$CH_2COO$—t-butyl | COOEt<br>\|<br>$NHCH(CH_2)_2$—2 or 3-(1-methylindolyl) |
| H | 1 | —$CH_2COOEt$ | COOEt<br>\|<br>$NHCH(CH_2)_2$—2 or 3-(1-methylindolyl) |
| H | 1 | Ph | COOEt<br>\|<br>$NHCH(CH_2)_2$—2 or 3-(1-methylindolyl) |
| H | 1 | o-F—Ph | $NHCH(CH_2)_2$—2 or 3-indolyl-<br>\|<br>COO—t-Butyl |
| H | 1 | —$CH_2COO$—t-butyl | $NHCH(CH_2)_2$—2 or 3-indolyl-<br>\|<br>COO—t-Butyl |
| H | 1 | —$CH_2COOEt$ | $NHCH(CH_2)_2$—2 or 3-indolyl-<br>\|<br>COO—t-Butyl |
| H | 1 | Ph | $NHCH(CH_2)_2$—2 or 3-indolyl-<br>\|<br>COO—t-Butyl |

TABLE 3-continued

Compounds of the formula:

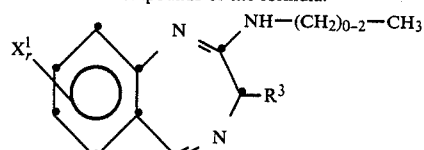

| $X^1$ | r | $R^2$ | $R^3$ |
|---|---|---|---|
| H | 1 | o-F—Ph | COO—t-Butyl<br>\|<br>$NHCH(CH_2)_2$—2 or 3-(1-methylindolyl) |
| H | 1 | —$CH_2COO$—t-butyl | COO—t-Butyl<br>\|<br>$NHCH(CH_2)_2$—2 or 3-(1-methylindolyl) |
| H | 1 | —$CH_2COOEt$ | COO—t-Butyl<br>\|<br>$NHCH(CH_2)_2$—2 or 3-(1-methylindolyl) |
| H | 1 | Ph | COO—t-Butyl<br>\|<br>$NHCH(CH_2)_2$—2 or 3-(1-methylindolyl) |

TABLE 4

Compounds of the formula:

| $X^1$ | r | $R^2$ | $R^3$ |
|---|---|---|---|
| H | 1 | o-F—Ph | —$CH_2$—2-indolyl |
| H | 1 | o-F—Ph | —$CH_2$—3-indolyl |
| H | 1 | o-F—Ph— | $NH(CH_2)_{1-3}$—3-indolyl |
| H | 1 | o-F—Ph | —$NHCH_2$—$(CH_2)_2$—3-indolyl<br>COOEt |
| H | 1 | o-F—Ph | —$CH_2NH(CH_2)_2$—3-indolyl |
| H | 1 | o-F—Ph | —$NHCO$—$(CH_2)_{0-2}$—2-indolyl |
| H | 1 | o-F—Ph | —$NHCO(CH_2)_{0-2}$—3-indolyl |
| H | 1 | o-F—Ph | NHCO—p-halo-phenyl |
| H | 1 | o-F—Ph | NHCO—m-halo-phenyl |
| H | 1 | o-F—Ph | NHCO—2-benzofuranyl |
| H | 1 | o-F—Ph | 2-(3-methylindenyl) |
| H | 1 | o-F—Ph | phenylethenyl |
| H | 1 | o-F—Ph | NHCONH—p-halo-phenyl |
| H | 1 | p-Cl—Ph | —$CH_2$—2-indolyl |
| H | 1 | p-Cl—Ph | —$CH_2$—3-indolyl |
| H | 1 | p-Cl—Ph | —$NH(CH_2)_{1-3}$—3-indolyl |
| H | 1 | p-Cl—Ph | —$NHCO$—$(CH_2)_{0-2}$—2-indolyl |
| H | 1 | p-Cl—Ph | NHCO—p-halo-phenyl |
| H | 1 | p-Cl—Ph | NHCO—m-halo-phenyl |
| H | 1 | p-Cl—Ph | NHCO—2-benzofuranyl |
| H | 1 | p-Cl—Ph | 2-(3-methylindenyl) |
| H | 1 | p-Cl—Ph | phenylethenyl |
| H | 1 | p-Cl—Ph | NHCONH—p-halo-phenyl |
| H | 1 | phenyl | —$CH_2$—2-indolyl |
| H | 1 | phenyl | —$CH_2$—3-indolyl |
| H | 1 | phenyl | —$NHCO(CH_2)_{0-2}$—3-indolyl |
| H | 1 | phenyl | —$NH(CH_2)_{1-3}$—3-indolyl |
| H | 1 | phenyl | NHCO—p-halo-phenyl |
| H | 1 | phenyl | NHCO—m-halo-phenyl |
| H | 1 | phenyl | NHCO—2-benzofuranyl |
| H | 1 | phenyl | 2-(3-methylindenyl) |
| H | 1 | phenyl | phenylethenyl |

TABLE 4-continued

Compounds of the formula:

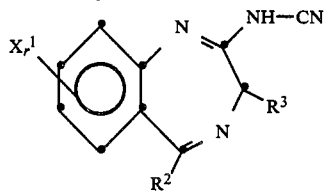
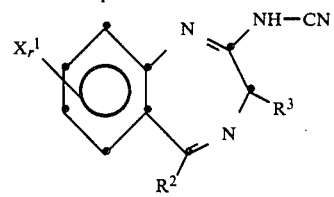

| $X_r^1$ | r | $R^2$ | $R^3$ |
|---|---|---|---|
| H | 1 | phenyl | NHCONH—p-halo-phenyl |
| H | 1 | p-F—Ph | —CH$_2$—2-indolyl |
| H | 1 | p-F—Ph | —CH$_2$—3-indolyl |
| H | 1 | p-F—Ph | —NHCO(CH$_2$)$_{0-2}$—2-indolyl |
| H | 1 | p-F—Ph | —NH(CH$_2$)$_{1-3}$—3-indolyl |
| H | 1 | p-F—Ph | NHCO—p-halo-phenyl |
| H | 1 | p-F—Ph | NHCO—m-halo-phenyl |
| H | 1 | p-F—Ph | NHCO—2-benzofuranyl |
| H | 1 | p-F—Ph | 2-(3-methylindenyl) |
| H | 1 | p-F—Ph | phenylethenyl |
| H | 1 | p-F—Ph | NHCONH—p-halo-phenyl |
| H | 1 | 2,4-di-Cl—Ph | —CH$_2$—2-indolyl |
| H | 1 | 2,4-di-Cl—Ph | —CH$_2$—3-indolyl |
| H | 1 | 2,4-di-Cl—Ph | —NHCO(CH$_2$)$_{0-2}$—2-indolyl |
| H | 1 | 2,4-di-Cl—Ph | —NH(CH$_2$)$_{1-3}$—3-indolyl |
| H | 1 | 2,4-di-Cl—Ph | NHCO—p-halo-phenyl |
| H | 1 | 2,4-di-Cl—Ph | NHCO—m-halo-phenyl |
| H | 1 | 2,4-di-Cl—Ph | NHCO—2-benzofuranyl |
| H | 1 | 2,4-di-Cl—Ph | 2-(3-methylindenyl) |
| H | 1 | 2,4-di-Cl—Ph | phenylethenyl |
| H | 1 | 2,4-di-Cl—Ph | NHCONH—p-halo-phenyl |
| H | 1 | 2,6-di-F—Ph | —CH$_2$—2-indolyl |
| H | 1 | 2,6-di-F—Ph | —CH$_2$—3-indolyl |
| H | 1 | 2,6-di-F—Ph | —NHCO(CH$_2$)$_{0-2}$—2-indolyl |
| H | 1 | 2,6-di-F—Ph | —NH(CH$_2$)$_{1-3}$—3-indolyl |
| H | 1 | 2,6-di-F—Ph | NHCO—p-halo-phenyl |
| H | 1 | 2,6-di-F—Ph | NHCO—m-halo-phenyl |
| H | 1 | 2,6-di-F—Ph | NHCO—2-benzofuranyl |
| H | 1 | 2,6-di-F—Ph | 2-(3-methylindenyl) |
| H | 1 | 2,6-di-F—Ph | phenylethenyl |
| H | 1 | 2,6-di-F—Ph | NHCONH—p-halo-phenyl |
| H | 1 | CH$_2$COO—t-butyl | —CH$_2$—2-indolyl |
| H | 1 | CH$_2$COO—t-butyl | —CH$_2$—3-indolyl |
| H | 1 | CH$_2$COO—t-butyl | —NHCO(CH$_2$)$_{0-2}$—3-indolyl |
| H | 1 | CH$_2$COO—t-butyl | —NH(CH$_2$)$_{1-3}$—3-indolyl |
| H | 1 | CH$_2$COO—t-butyl | NHCO—p-halo-phenyl |
| H | 1 | CH$_2$COO—t-butyl | NHCO—m-halo-phenyl |
| H | 1 | CH$_2$COO—t-butyl | NHCO—2-benzofuranyl |
| H | 1 | CH$_2$COO—t-butyl | 2-(3-methylindenyl) |
| H | 1 | CH$_2$COO—t-butyl | phenylethenyl |
| H | 1 | CH$_2$COO—t-butyl | NHCONH—p-halo-phenyl |
| H | 1 | —CH$_2$COOEt | —CH$_2$—2-indolyl |
| H | 1 | —CH$_2$COOEt | —CH$_2$—3-indolyl |
| H | 1 | —CH$_2$COOEt | —NHCO(CH$_2$)$_{0-2}$—3-indolyl |
| H | 1 | —CH$_2$COOEt | —NH(CH$_2$)$_{1-3}$—3-indolyl |
| H | 1 | —CH$_2$COOEt | NHCO—p-halo-phenyl |
| H | 1 | —CH$_2$COOEt | NHCO—m-halo-phenyl |
| H | 1 | —CH$_2$COOEt | NHCO—2-benzofuranyl |
| H | 1 | —CH$_2$COOEt | 2-(3-methylindenyl) |
| H | 1 | —CH$_2$COOEt | phenylethenyl |
| H | 1 | —CH$_2$COOEt | NHCONH—p-halo-phenyl |
| Cl | 1 | p-Cl—Ph | —CH$_2$—2-indolyl |
| Cl | 1 | p-Cl—Ph | —CH$_2$—3-indolyl |
| Cl | 1 | p-Cl—Ph | —NHCO(CH$_2$)$_{0-2}$—2-indolyl |
| Cl | 1 | p-Cl—Ph | —NH(CH$_2$)$_{1-3}$—3-indolyl |
| Cl | 1 | p-Cl—Ph | NHCO—p-halo-phenyl |
| Cl | 1 | p-Cl—Ph | NHCO—m-halo-phenyl |
| Cl | 1 | p-Cl—Ph | NHCO—2-benzofuranyl |
| Cl | 1 | p-Cl—Ph | 2-(3-methylindenyl) |
| Cl | 1 | p-Cl—Ph | phenylethenyl |
| Cl | 1 | p-Cl—Ph | NHCONH—p-halo-phenyl |
| Cl | 1 | Ph | —CH$_2$—2-indolyl |
| Cl | 1 | Ph | —CH$_2$—3-indolyl |
| Cl | 1 | Ph | —NHCO(CH$_2$)$_{0-2}$—2-indolyl |
| Cl | 1 | Ph | —NH(CH$_2$)$_{1-3}$—3-indolyl |
| Cl | 1 | Ph | NHCO—p-halo-phenyl |
| Cl | 1 | Ph | NHCO—m-halo-phenyl |
| Cl | 1 | Ph | NHCO—2-benzofuranyl |
| Cl | 1 | Ph | 2-(3-methylindenyl) |
| Cl | 1 | Ph | phenylethenyl |
| Cl | 1 | Ph | NHCONH—p-halo-phenyl |
| Cl | 1 | o-F—Ph | —CH$_2$—2-indolyl |
| Cl | 1 | o-F—Ph | —CH$_2$—3-indolyl |
| Cl | 1 | o-F—Ph | —NHCO(CH$_2$)$_{0-2}$—2-indolyl |
| Cl | 1 | o-F—Ph | —NH(CH$_2$)$_{1-3}$—3-indolyl |
| Cl | 1 | o-F—Ph | NHCO—p-halo-phenyl |
| Cl | 1 | o-F—Ph | NHCO—m-halo-phenyl |
| Cl | 1 | o-F—Ph | NHCO—2-benzofuranyl |
| Cl | 1 | o-F—Ph | 2-(3-methylindenyl) |
| Cl | 1 | o-F—Ph | phenylethenyl |
| Cl | 1 | o-F—Ph | NHCONH—p-halo-phenyl |
| Cl | 1 | p-F—Ph | —CH$_2$—2-indolyl |
| Cl | 1 | p-F—Ph | —CH$_2$—3-indolyl |
| Cl | 1 | p-F—Ph | —NHCO(CH$_2$)$_{0-2}$—2-indolyl |
| Cl | 1 | p-F—Ph | —NH(CH$_2$)$_{1-3}$—3-indolyl |
| Cl | 1 | p-F—Ph | NHCO—p-halo-phenyl |
| Cl | 1 | p-F—Ph | NHCO—m-halo-phenyl |
| Cl | 1 | p-F—Ph | NHCO—2-benzofuranyl |
| Cl | 1 | p-F—Ph | 2-(3-methylindenyl) |
| Cl | 1 | p-F—Ph | phenylethenyl |
| Cl | 1 | p-F—Ph | NHCONH—p-halo-phenyl |
| F | 1 | 2,4-di-Cl—Ph | —CH$_2$—2-indolyl |
| F | 1 | 2,4-di-Cl—Ph | —CH$_2$—3-indolyl |
| F | 1 | 2,4-di-Cl—Ph | —NHCO(CH$_2$)$_{0-2}$—2-indolyl |
| F | 1 | 2,4-di-Cl—Ph | —NH(CH$_2$)$_{1-3}$—3-indolyl |
| F | 1 | 2,4-di-Cl—Ph | NHCO—p-halo-phenyl |
| F | 1 | 2,4-di-Cl—Ph | NHCO—m-halo-phenyl |
| F | 1 | 2,4-di-Cl—Ph | NHCO—2-benzofuranyl |
| F | 1 | 2,4-di-Cl—Ph | 2-(3-methylindenyl) |
| F | 1 | 2,4-di-Cl—Ph | phenylethenyl |
| F | 1 | 2,4-di-Cl—Ph | NHCONH—p-halo-phenyl |
| F | 1 | 2,6-di-F—Ph | —CH$_2$—2-indolyl |
| F | 1 | 2,6-di-F—Ph | —CH$_2$—3-indolyl |
| F | 1 | 2,6-di-F—Ph | —NHCO(CH$_2$)$_{0-2}$—2-indolyl |
| F | 1 | 2,6-di-F—Ph | —NH(CH$_2$)$_{1-3}$—3-indolyl |
| F | 1 | 2,6-di-F—Ph | NHCO—p-halo-phenyl |
| F | 1 | 2,6-di-F—Ph | NHCO—m-halo-phenyl |
| F | 1 | 2,6-di-F—Ph | NHCO—2-benzofuranyl |
| F | 1 | 2,6-di-F—Ph | 2-(3-methylindenyl) |
| F | 1 | 2,6-di-F—Ph | phenylethenyl |
| F | 1 | 2,6-di-F—Ph | NHCONH—p-halo-phenyl |
| F | 1 | COO—t-butyl | —CH$_2$—2-indolyl |
| F | 1 | COO—t-butyl | —CH$_2$—3-indolyl |
| F | 1 | COO—t-butyl | —NHCO(CH$_2$)$_{0-2}$—2-indolyl |
| F | 1 | COO—t-butyl | —NH(CH$_2$)$_{1-3}$—3-indolyl |
| F | 1 | COO—t-butyl | NHCO—p-halo-phenyl |
| F | 1 | COO—t-butyl | NHCO—m-halo-phenyl |
| F | 1 | COO—t-butyl | NHCO—2-benzofuranyl |
| F | 1 | COO—t-butyl | 2-(3-methylindenyl) |
| F | 1 | COO—t-butyl | phenylethenyl |
| F | 1 | COO—t-butyl | NHCONH—p-halo-phenyl |
| F | 1 | —CH$_2$COOEt | —CH$_2$—2-indolyl |
| F | 1 | —CH$_2$COOEt | —CH$_2$—3-indolyl |
| F | 1 | —CH$_2$COOEt | —NHCO(CH$_2$)$_{0-2}$—2-indolyl |
| F | 1 | —CH$_2$COOEt | —NH(CH$_2$)$_{1-3}$—3-indolyl |
| F | 1 | —CH$_2$COOEt | NHCO—p-halo-phenyl |
| F | 1 | —CH$_2$COOEt | NHCO—m-halo-phenyl |
| F | 1 | —CH$_2$COOEt | NHCO—2-benzofuranyl |
| F | 1 | —CH$_2$COOEt | 2-(3-methylindenyl) |
| F | 1 | —CH$_2$COOEt | phenylethenyl |
| F | 1 | —CH$_2$COOEt | NHCONH—p-halo-phenyl |
| CF$_3$ | 1 | p-Cl—Ph | —CH$_2$—2-indolyl |
| CF$_3$ | 1 | p-Cl—Ph | —CH$_2$—3-indolyl |
| CF$_3$ | 1 | p-Cl—Ph | —NHCO(CH$_2$)$_{0-2}$—2-indolyl |
| CF$_3$ | 1 | p-Cl—Ph | —NH(CH$_2$)$_{1-3}$—3-indolyl |
| CF$_3$ | 1 | p-Cl—Ph | NHCO—p-halo-phenyl |
| CF$_3$ | 1 | p-Cl—Ph | NHCO—m-halo-phenyl |
| CF$_3$ | 1 | p-Cl—Ph | NHCO—2-benzofuranyl |
| CF$_3$ | 1 | p-Cl—Ph | 2-(3-methylindenyl) |
| CF$_3$ | 1 | p-Cl—Ph | phenylethenyl |

TABLE 4-continued

Compounds of the formula:

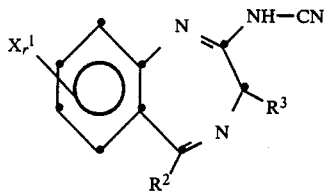
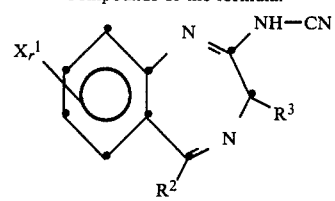

| X¹ | r | R² | R³ |
|---|---|---|---|
| $CF_3$ | 1 | p-Cl—Ph | NHCONH—p-halo-phenyl |
| $CF_3$ | 1 | Ph | —$CH_2$—2-indolyl |
| $CF_3$ | 1 | Ph | —$CH_2$—3-indolyl |
| $CF_3$ | 1 | Ph | —NHCO$(CH_2)_{0-2}$—2-indolyl |
| $CF_3$ | 1 | Ph | —NH$(CH_2)_{1-3}$—3-indolyl |
| $CF_3$ | 1 | Ph | NHCO—p-halo-phenyl |
| $CF_3$ | 1 | Ph | NHCO—m-halo-phenyl |
| $CF_3$ | 1 | Ph | NHCO—2-benzofuranyl |
| $CF_3$ | 1 | Ph | 2-(3-methylindenyl) |
| $CF_3$ | 1 | Ph | phenylethenyl |
| $CF_3$ | 1 | Ph | NHCONH—p-halo-phenyl |
| $CF_3$ | 1 | o-F—Ph | —$CH_2$—2-indolyl |
| $CF_3$ | 1 | o-F—Ph | —$CH_2$—3-indolyl |
| $CF_3$ | 1 | o-F—Ph | —NHCO$(CH_2)_{0-2}$—2-indolyl |
| $CF_3$ | 1 | o-F—Ph | —NH$(CH_2)_{1-3}$—3-indolyl |
| $CF_3$ | 1 | o-F—Ph | NHCO—p-halo-phenyl |
| $CF_3$ | 1 | o-F—Ph | NHCO—m-halo-phenyl |
| $CF_3$ | 1 | o-F—Ph | NHCO—2-benzofuranyl |
| $CF_3$ | 1 | o-F—Ph | 2-(3-methylindenyl) |
| $CF_3$ | 1 | o-F—Ph | phenylethenyl |
| $CF_3$ | 1 | o-F—Ph | NHCONH—p-halo-phenyl |
| $CF_3$ | 1 | p-F—Ph | —$CH_2$—2-indolyl |
| $CF_3$ | 1 | p-F—Ph | —$CH_2$—3-indolyl |
| $CF_3$ | 1 | p-F—Ph | —NHCO$(CH_2)_{0-2}$—2-indolyl |
| $CF_3$ | 1 | p-F—Ph | —NH$(CH_2)_{1-3}$—3-indolyl |
| $CF_3$ | 1 | p-F—Ph | NHCO—p-halo-phenyl |
| $CF_3$ | 1 | p-F—Ph | NHCO—m-halo-phenyl |
| $CF_3$ | 1 | p-F—Ph | NHCO—2-benzofuranyl |
| $CF_3$ | 1 | p-F—Ph | 2-(3-methylindenyl) |
| $CF_3$ | 1 | p-F—Ph | phenylethenyl |
| $CF_3$ | 1 | p-F—Ph | NHCONH—p-halo-phenyl |
| $NO_2$ | 1 | p-Cl—Ph | —$CH_2$—2-indolyl |
| $NO_2$ | 1 | p-Cl—Ph | —$CH_2$—3-indolyl |
| $NO_2$ | 1 | p-Cl—Ph | —NHCO$(CH_2)_{0-2}$—2-indolyl |
| $NO_2$ | 1 | p-Cl—Ph | —NH$(CH_2)_{1-3}$—3-indolyl |
| $NO_2$ | 1 | p-Cl—Ph | NHCO—p-halo-phenyl |
| $NO_2$ | 1 | p-Cl—Ph | NHCO—m-halo-phenyl |
| $NO_2$ | 1 | p-Cl—Ph | NHCO—2-benzofuranyl |
| $NO_2$ | 1 | p-Cl—Ph | 2-(3-methylindenyl) |
| $NO_2$ | 1 | p-Cl—Ph | phenylethenyl |
| $NO_2$ | 1 | p-Cl—Ph | NHCONH—p-halo-phenyl |
| $NO_2$ | 1 | Ph | —$CH_2$—2-indolyl |
| $NO_2$ | 1 | Ph | —$CH_2$—3-indolyl |
| $NO_2$ | 1 | Ph | —NHCO$(CH_2)_{0-2}$—2-indolyl |
| $NO_2$ | 1 | Ph | NHCO—p-halo-phenyl |
| $NO_2$ | 1 | Ph | NHCO—m-halo-phenyl |
| $NO_2$ | 1 | Ph | NHCO—2-benzofuranyl |
| $NO_2$ | 1 | Ph | 2-(3-methylindenyl) |
| $NO_2$ | 1 | Ph | phenylethenyl |
| $NO_2$ | 1 | Ph | NHCONH—p-halo-phenyl |
| $NO_2$ | 1 | o-F—Ph | —$CH_2$—2-indolyl |
| $NO_2$ | 1 | o-F—Ph | —$CH_2$—3-indolyl |
| $NO_2$ | 1 | o-F—Ph | —NHCO$(CH_2)_{0-2}$—2-indolyl |
| $NO_2$ | 1 | o-F—Ph | —NH$(CH_2)_{1-3}$—3-indolyl |
| $NO_2$ | 1 | o-F—Ph | NHCO—p-halo-phenyl |
| $NO_2$ | 1 | o-F—Ph | NHCO—m-halo-phenyl |
| $NO_2$ | 1 | o-F—Ph | NHCO—2-benzofuranyl |
| $NO_2$ | 1 | o-F—Ph | 2-(3-methylindenyl) |
| $NO_2$ | 1 | o-F—Ph | phenylethenyl |
| $NO_2$ | 1 | o-F—Ph | NHCONH—p-halo-phenyl |
| $NO_2$ | 1 | p-F—Ph | —$CH_2$—2-indolyl |
| $NO_2$ | 1 | p-F—Ph | —$CH_2$—3-indolyl |
| $NO_2$ | 1 | p-F—Ph | —NHCO$(CH_2)_{0-2}$—2-indolyl |
| $NO_2$ | 1 | p-F—Ph | —NH$(CH_2)_{1-3}$—3-indolyl |
| $NO_2$ | 1 | p-F—Ph | NHCO—p-halo-phenyl |
| $NO_2$ | 1 | p-F—Ph | NHCO—m-halo-phenyl |
| $NO_2$ | 1 | p-F—Ph | NHCO—2-benzofuranyl |
| $NO_2$ | 1 | p-F—Ph | 2-(3-methylindenyl) |
| $NO_2$ | 1 | p-F—Ph | phenylethenyl |
| $NO_2$ | 1 | p-F—Ph | NHCONH—p-halo-phenyl |
| $CH_3$ | 1 | phenyl | —$CH_2$—2-indolyl |
| $CH_3$ | 1 | phenyl | —$CH_2$—3-indolyl |
| $CH_3$ | 1 | phenyl | —NHCO$(CH_2)_{0-2}$—2-indolyl |
| $CH_3$ | 1 | phenyl | —NH$(CH_2)_{1-3}$—3-indolyl |
| $CH_3$ | 1 | phenyl | NHCO—p-halo-phenyl |
| $CH_3$ | 1 | phenyl | NHCO—m-halo-phenyl |
| $CH_3$ | 1 | phenyl | NHCO—2-benzofuranyl |
| $CH_3$ | 1 | phenyl | 2-(3-methylindenyl) |
| $CH_3$ | 1 | phenyl | phenylethenyl |
| $CH_3$ | 1 | phenyl | NHCONH—p-halo-phenyl |
| H | 1 | o-F—Ph | —$CH_2$—2-indolyl |
| H | 1 | o-F—Ph | —$CH_2$—3-indolyl |
| H | 1 | o-F—Ph | —NHCO$(CH_2)_{0-2}$—2-indolyl |
| H | 1 | o-F—Ph | —NH$(CH_2)_{1-3}$—3-indolyl |
| H | 1 | o-F—Ph | NHCO—p-halo-phenyl |
| H | 1 | o-F—Ph | NHCO—m-halo-phenyl |
| H | 1 | o-F—Ph | NHCO—2-benzofuranyl |
| H | 1 | o-F—Ph | 2-(3-methylindenyl) |
| H | 1 | o-F—Ph | phenylethenyl |
| H | 1 | o-F—Ph | NHCONH—p-halo-phenyl |
| H | 1 | p-Cl—Ph | —$CH_2$—2-indolyl |
| H | 1 | p-Cl—Ph | —$CH_2$—3-indolyl |
| H | 1 | p-Cl—Ph | —NHCO$(CH_2)_{0-2}$—2-indolyl |
| H | 1 | p-Cl—Ph | —NH$(CH_2)_{1-3}$—3-indolyl |
| H | 1 | P-Cl—Ph | NHCO—p-halo-phenyl |
| H | 1 | P-Cl—Ph | NHCO—m-halo-phenyl |
| H | 1 | P-Cl—Ph | NHCO—2-benzofuranyl |
| H | 1 | P-Cl—Ph | 2-(3-methylindenyl) |
| H | 1 | P-Cl—Ph | phenylethenyl |
| H | 1 | P-Cl—Ph | NHCONH—p-halo-phenyl |
| H | 1 | o-F—Ph | $CH_2$—2 or 3-(1-methylindolyl) |
| H | 1 | —$CH_2$COO—t-butyl | $CH_2$—2 or 3-(1-methylindolyl) |
| H | 1 | —$CH_2$COOEt | $CH_2$—2 or 3-(1-methylindolyl) |
| H | 1 | Ph | $CH_2$—2 or 3-(1-methylindolyl) |
| H | 1 | o-F—Ph | NHCO$(CH_2)_{0-2}$—2-indolyl |
| H | 1 | —$CH_2$COO—t-butyl | NHCO$(CH_2)_{0-2}$—2-indolyl |
| H | 1 | —$CH_2$COOEt | NHCO$(CH_2)_{0-2}$—2-indolyl |
| H | 1 | Ph | NHCO$(CH_2)_{0-2}$—2-indolyl |
| H | 1 | o-F—Ph | NHCO$(CH_2)_{0-2}$—2 or 3-(1-methylindolyl) |
| H | 1 | —$CH_2$COO—t-butyl | NHCO$(CH_2)_{0-2}$—2 or 3-(1-methylindolyl) |
| H | 1 | —$CH_2$COOEt | NHCO$(CH_2)_{0-2}$—2 or 3-(1-methylindolyl) |
| H | 1 | Ph | NHCO$(CH_2)_{0-2}$—2 or 3-(1-methylindolyl) |
| H | 1 | o-F—Ph | NH$(CH_2)_{1-3}$—2-indolyl |
| H | 1 | —$CH_2$COO—t-butyl | NH$(CH_2)_{1-3}$—2-indolyl |
| H | 1 | —$CH_2$COOEt | NH$(CH_2)_{1-3}$—2-indolyl |
| H | 1 | Ph | NH$(CH_2)_{1-3}$—2-indolyl |
| H | 1 | o-F—Ph | NH$(CH_2)_{1-3}$—2 or 3-(1-methylindolyl) |
| H | 1 | —$CH_2$COO—t-butyl | NH$(CH_2)_{1-3}$—2 or 3-(1-methylindolyl) |
| H | 1 | —$CH_2$COOEt | NH$(CH_2)_{1-3}$—2 or 3-(1-methylindolyl) |
| H | 1 | Ph | NH$(CH_2)_{1-3}$—2 or 3-(1-methylindolyl) |
| H | 1 | o-F—Ph | NHCH$(CH_2)_2$—2-indolyl<br>\|<br>COOEt |
| H | 1 | —$CH_2$COO—t-butyl | NHCH$(CH_2)_2$—2-indolyl<br>\|<br>COOEt |

TABLE 4-continued

Compounds of the formula:

[Structure: benzodiazepine with X₁ substituent on benzene ring, N=C(NH-CN) group, and R² on CH and R³ on N]

| X¹ | r | R² | R³ |
|---|---|---|---|
| H | 1 | —CH₂COOEt | NHCH(CH₂)₂—2-indolyl<br>\|<br>COOEt |
| H | 1 | Ph | NHCH(CH₂)₂—2-indolyl<br>\|<br>COOEt |
| H | 1 | o-F—Ph | COOEt<br>\|<br>NHCH(CH₂)₂—2 or<br>3-(1-methylindolyl) |
| H | 1 | —CH₂COO—t-butyl | COOEt<br>\|<br>NHCH(CH₂)₂—2 or<br>3-(1-methylindolyl) |
| H | 1 | —CH₂COOEt | COOEt<br>\|<br>NHCH(CH₂)₂—2 or<br>3-(1-methylindolyl) |
| H | 1 | Ph | COOEt<br>\|<br>NHCH(CH₂)₂—2 or<br>3-(1-methylindolyl) |
| H | 1 | o-F—Ph | NHCH(CH₂)₂—2 or 3-indolyl-<br>\|<br>COO—t-Butyl |
| H | 1 | —CH₂COO—t-butyl | NHCH(CH₂)₂—2 or 3-indolyl-<br>\|<br>COO—t-Butyl |
| H | 1 | —CH₂COOEt | NHCH(CH₂)₂—2 or 3-indolyl-<br>\|<br>COO—t-Butyl |
| H | 1 | Ph | NHCH(CH₂)₂—2 or 3-indolyl-<br>\|<br>COO—t-Butyl |
| H | 1 | o-F—Ph | COO—t-Butyl<br>\|<br>NHCH(CH₂)₂—2 or<br>3-(1-methylindolyl) |
| H | 1 | —CH₂COO—t-butyl | COO—t-Butyl<br>\|<br>NHCH(CH₂)₂—2 or<br>3-(1-methylindolyl) |
| H | 1 | —CH₂COOEt | COO—t-Butyl<br>\|<br>NHCH(CH₂)₂—2 or<br>3-(1-methylindolyl) |
| H | 1 | Ph | COO—t-Butyl<br>\|<br>NHCH(CH₂)₂—2 or<br>3-(1-methylindolyl) |

The invention is further defined by reference to the following preparations and examples, which are intended to be illustrative and not limiting.

All temperatures are in degrees Celsius.

PREPARATION 1

1,3-Dihydro-3(R)-(3'-indolyl)methyl-5-(2'-fluorophenyl)-2H-1,4-benzodiazepin-2-thione 1,3-Dihydro-3(R)-(3'-indolyl)methyl-5-(2'-fluorophenyl)-2H-1,4-benzodiazepin-2-one (6.98 g, 18.20 mmole) was refluxed with 4.41 g (10.92 mmole) of 2,4-bis-(4-methoxyphenyl)-2,4-dithioxo-1,3,2,4-dithiadiphosphetane in 100 ml of toluene for 1.5 hours. The solvent was removed in vacuo and the residue partitioned between ethyl acetate and 10% sodium hydroxide solution. The organic phase was washed with 10% sodium hydroxide (3×50 ml) and brine, then dried (MgSO₄) and rotoevaporated to give an orange oil (10 g). Plug filtration of the crude product through silica gel (100 g) afforded a solid which was recrystallized from ether to afford the analytical sample as an ether solvate. m.p. 147°–148° C. Pmr confirmed the structure of the title compound.

EXAMPLE 1

2-Phenylamino-3(R)-(3'-indolyl)methyl-5-(2'-fluorophenyl)-2H-1,4-benzodiazepine 2-Methylthio-3(R)-(3'-indolyl)methyl-5-(2'-fluorophenyl)-2H-1,4-benzodiazepine (170 mg, 0.42 mmole) was mixed with 138 µl (3.6 equivalents) of aniline and the whole immersed in a preheated bath at 80° C. After 2 days, the dark reaction mixture was chromatographed on silica gel (hexane-ethyl acetate elution 2:1 v/v) to give the analytical sample as an off-white solid, m.p. 127°.

TLC, HPLC: greater than 98% pure.
MS (20 ev): 458 (M+), 366, 329, 130.
Pmr (CDCl₃): Confirmed the structure of the title compound.
Elemental Analysis: $C_{30}H_{23}FN_4O.2H_2O$: Calc'd: N, 12.12; C, 77.96; H, 5.10. Found: N, 12.22; C, 77.89; H, 4.93.

EXAMPLE 2

2-Methylthio-3(R)-(3'-indolyl)methyl-5-(2'-fluorophenyl)2H-1,4-benzodiazepine Thioamide according to Preparation 1 (2.66 g, 6.66 mmole) was added to a suspension of 40% sodium hydroxide solution (30 ml), 50 ml of toluene, 25 ml of tetrahydrofuran, and 10 ml of water. The reaction mixture was then treated with 1.49 g (0.66 equivalents) of tetra-n-butyl ammonium sulfate. After 5 minutes, 456 µl (1.1 equivalents) of iodomethane was added to the rapidly stirred suspension. The reaction was stirred at room temperature for 15 minutes more, poured into a separatory funnel and the phases separated. The organic phase was washed with water and brine, then dried (MgSO₄) and concentrated to yield 2.8 g of the crude product. The analytical sample was obtained via flash column chromatography on silica gel (hexane-ethyl acetate elution, 2:1 v/v).

TLC, HPLC: greater than 97.9% pure.
MS (20 ev): 413 (M+), 284, 130.
Pmr (CDCl₃): Spectrum according to theory. SCH₃ (2.49 ppm)
Elemental Analysis: $C_{25}H_{20}FN_3OS0.3H_2O$: Calc'd: N, 10.03; C, 71.67; H, 4.95. Found: N, 9.84; C, 71.74; H, 4.66.

EXAMPLE 3

2-Amino-3(R)-(3'-indolyl)methyl-5-(2'-fluorophenyl)-2H-1,4-benzodiazepine

Thioamide according to Preparation 1 (170 mg, 0.43 mmole) was dissolved in warm methanol (6 ml). Concentrated ammonium hydroxide solution (58%) (2 ml) was added followed by 117 mg (0.43 mmole) of mercuric chloride. The reaction mixture was stirred vigorously for 3 hours, cooled and filtered through Celite. The filtrate was concentrated to dryness and the resulting white solid (200 mg) chromatographed on silica gel (chloroform-ethanol-ammonia, 90:10:1 v/v) to give the analytical product (120 mg).

TLC, HPLC: greater than 98% pure.
MS (20 ev): 382 (M+), 253, 211, 130.
Pmr (CDCl$_3$): Confirmed the structure of the title compound.
$^{19}$F nmr (CD$_3$OD): 113 ppm
Elemental Analysis: C$_{24}$H$_{19}$FN$_4$0.25H$_2$O: Calc'd: N, 14.48; C, 74.49; H, 5.07. Found: N, 14.72; C, 74.41; H, 4.92.

EXAMPLE 4

2-Methylamino-3(R)-(3'-indolyl)methyl-5-(2'-fluorophenyl)-2H-1,4-benzodiazepine

This compound was prepared according to Example 3 using 2 g (5 mmole) of thioamide according to Preparation 1, 2 g (7.4 mmole) of mercuric chloride, and 20 equivalents of methylamine in 30 ml of dry tetrahydrofuran. Yield of crude product=2.05 g as a white powder. TLC, HPLC: greater than 95% pure MS (14 ev): 396 (M+), 277, 211.
Pmr (CDCl$_3$): Confirmed the structure of the title compound; N-methyl protons resonate as a doublet at 2.94 ppm.
Elemental Analysis: C$_{25}$H$_{21}$FN$_4$0.2CHCl$_3$: Calc'd: N, 13.33; C, 72.00; H, 5.08. Found: N, 13.11; C, 72.08; H, 5.26.

EXAMPLE 5

2-Ethoxycarbonylmethylamino-3(R)-(3'-indolyl)methyl-5-(2'-fluorophenyl)-2H-1,4-benzodiazepine This compound was prepared according to Example 3 using 300 mg (0.75 mmole) of thioamide according to Preparation 1, 310 mg (1.13 mmole) of mercuric chloride and four equivalents of glycine ethyl ester in 25 ml of dry tetrahydrofuran. Work-up afforded 400 mg of crude product. The analytical sample was obtained via silica gel chromatography (chloroform-methanol 99:1 v/v).

HPLC, TLC: greater than 92% pure.
Pmr (CDCl$_3$): Confirmed the structure of the title compound.
MS (14 ev): 468 (M+), 422, 339.
Elemental Analysis: C$_{28}$H$_{25}$FN$_4$O$_2$0.1CHCl$_3$ Calc'd: N, 11.66; C, 70.24; H, 5.26. Found: N, 11.39; C, 70.46; H, 5.43.

EXAMPLE 6

2-Cyanoamino-3(R)-(3'-indolyl)methyl-5-(2'-fluorophenyl)-2H-1,4-benzodiazepine

This compound was prepared according to Example 3 using 300 mg (0.75 mmole) of thioamide according to Preparation 1, 310 mg (1.2 mmole) of mercuric chloride and 3 equivalents of cyanamide in 20 ml of dry tetrahydrofuran. Yield of crude product was 330 mg. Chromatography on silica gel using 1% methanol in chloroform gave the analytical sample. TLC, HPLC: greater than 96% pure.

MS (14 ev): 407 (M+), 378, 278.
Pmr (CDCl$_3$): Confirmed the structure of the title compound.
Elemental Analysis: C$_{25}$H$_{18}$FN$_5$1.05CHCl$_3$: Calc'd: N, 13.14; C, 58.71; H, 3.60. Found: N, 13.11; C, 58.59; H, 3.66.

EXAMPLE 7

2-Propylamino-3(R)-(3'-indolyl)methyl-5-(2-fluorophenyl)-2H-1,4-benzodiazepine 1,3-Dihydro-3(R)-(3'-indolyl)methyl-5-(2-fluorophenyl)-2H-1,4-benzodiazepin-2-thione (350 mg, 0.88 mmole) was dissolved in 20 ml of dry methanol. The solution was warmed to 50° C. and treated in succession with n-propylamine (1 ml, 12.2 mmole) and mercuric chloride (357 mg, 1.31 mmole). The reaction mixture was stirred at 50° C. for two hours during the course of which a black precipitate was deposited. The reaction mixture was filtered, concentrated in vacuo and the residue dissolved in ethyl acetate. The organic phase was washed with sodium thiosulfate solution (2×30 ml) and brine, then dried (MgSO$_4$) and concentrated to yield 400 mg of crude product. Silica gel chromatography of the crude product (hexane-acetone elution, 3:1 v/v) afforded the analytical sample.

TLC, HPLC: greater than 99.5% pure.
Pmr (CDCl$_3$): according to theory.
MS (14 ev): 424 (M+).
Elemental Analysis: C$_{27}$H$_{25}$FN$_4$.0.2H$_2$O: Calc'd: N, 13.08; C, 75.74; H, 5.98. Found: N, 12.56; C, 75.93; H, 6.26.

EXAMPLE 8

2-Carboxymethylamino-3(R)-(3'-indolyl)methyl-5-(2'-fluorophenyl)-2H-1,4-benzodiazepine To a solution of 1,3-dihydro-3(R)-(3'-indolyl)methyl-5-(2-fluorophenyl)-2H-1,4-benzodiazepin-2-thione (300 mg, 0.75 mmole) in 15 ml of dry tetrahydrofuran was added mercuric chloride (310 mg, 1.13 mmole) and glycine tert-butyl ester hydrochloride. The pH of the resulting suspension was adjusted to 8.5 with triethylamine and the reaction mixture was then heated at 55° C. for 2 hours. The reaction was cooled, filtered through a Celite pad and concentrated. The residual semi-solid was dissolved in ethyl acetate (150 ml) and washed with sodium thiosulfate solution (2×50 ml) and brine. The dried ((MgSO$_4$) organic phase was concentrated to yield 500 mg of crude product which was flash chromatographed on silica gel (hexane-ethyl acetate elution, 1:1 v/v) to remove polar biproducts. A portion of the purified intermediate ester (220 mg) was dissolved in 50 ml of ethyl acetate, cooled to 0° C. and treated with a continuous stream of hydrogen chloride gas for 30 minutes. The reaction mixture was then allowed to warm to room temperature and stand for 5 hours. Excess reagent and solvent were removed in vacuo to yield 200 mg of an orange-brown powder. The analytical material was obtained via silica gel chromatography (chloroform-methanol-acetic acid elution, 90:10:1 then 85:15:1.5 v/v) as an off-white powder (120 mg).

HPLC: greater than 96% pure.
Pmr (CD$_3$OD): according to theory.

MS (14 ev): 422 (M+-H$_2$O), 293, 277, 264, 246.

Elemental Analysis: C$_{26}$H$_{21}$FN$_4$O$_2$.0.8CHCl$_3$.0.8HOAc: Calc'd: N, 9.59; C, 58.40; H, 4.31. Found: N, 9.50; C, 58.31; H, 4.49.

EXAMPLE 9

N-[3-(((4-Chlorophenyl)aminocarbonyl)amino)-5-phenyl-3H-1,4-benzodiazepin-2-yl]-glycine Thioamide according to preparation 1 (80 mg, 0.20 mmole) was dissolved in dry tetrahydrofuran (5 ml). To this solution was added glycine t-butylester hydrochloride (134 mg, 0.80 mmole) and mercuric chloride (80 mg, 0.3 mmole). The pH of the reaction mixture was adjusted to approximately 8.5 with triethylamine and the reaction mixture was stirred at 55° C. for 3 hours. The reaction mixture was cooled, filtered and concentrated. The residue was partitioned between ethyl acetate and sodium thiosulfate solution. The organic phase was washed with brine and dried (Na$_2$SO$_4$). The dry ethyl acetate solution was then cooled to 0° C. and treated with a continuous stream of HCl gas for 30 minutes. The flask was stoppered and after 2 hours at room temperature, solvent and HCl gas were removed in vacuo. The residual solid was chromatographed on silica gel (CHCl$_3$-CH$_3$OH-AcOH elution, 90:10:1 v/v) to afford a solid which was triturated with methanol to give 26 mg of the analytical product: mp 186° C. (gas evolution).

TLC, HPLC: 98.9% pure.

MS (FAB): 462 (M+H).

PMR (DMSO-d$_6$): Confirms the structure assignment.

Elemental Analysis: C$_{24}$H$_{20}$ClN$_5$O$_3$.¼H$_2$O:Calc'd: C, 61.80; H, 4.43; N, 15.02. Found: C, 61.84; H, 4.59; N, 14.75.

EXAMPLE 10

N-[3-(((4-Chlorophenyl)aminocarbonyl)amino)-5-phenyl-3H-1,4-benzodiazepin-2-yl]-glycine ethyl ester Thioamide according to preparation 1 (100 mg, 0.25 mmole) was combined with glycine ethyl ester hydrochloride (140 mg, 1 mmole) and mercuric chloride (100 mg, 0.38 mmole). The pH of the reaction mixture was adjusted to approximately 8.5 with triethylamine. The reaction mixture was protected from moisture and cooled, filtered and the filtrate was concentrated to dryness. The residual solid was partitioned between ethyl acetate and sodium thiosulfate solution. The organic phase was washed with brine, dried (Na$_2$SO$_4$) and concentrated to give an oil. Preparative chromatography on silica gel (CHCl$_3$-CH$_3$OH-NH$_4$OH elution, 97:3:0.3 v/v) afforded 80 mg of the analytical product; recrystallization from ether gave shimmering crystals: mp 164°–165° C.

TLC, HPLC: Greater than 99.9% pure.

MS (FAB): 490 (M+H).

PMR (CDCl$_3$): Confirms structure assignment of product and ether solvate.

Elemental Analysis: C$_{26}$H$_{24}$ClN$_5$O$_3$.½C$_4$H$_{10}$O: Calc'd: C, 63.81; H, 5.55; N, 13.29. Found: C, 63.76; H, 5.39; N, 13.12.

Claims to the invention follow.

What is claimed is:

1. A compound of Formula I:

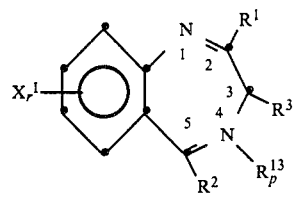

wherein

R$^1$ is —NR$^{16}$R$^{17}$;

R$^2$ is H, loweralkyl, substituted or unsubstituted phenyl (wherein the substituents are 1 or 2 of halo, loweralkyl, loweralkoxy, loweralkylthio, carboxyl, carboxyloweralkyl, nitro, —CF$_3$, or hydroxy), 2-, 3-, 4-pyridyl,

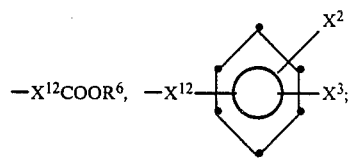

R$^3$ is

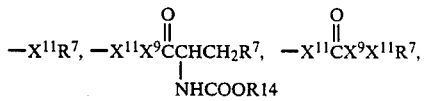

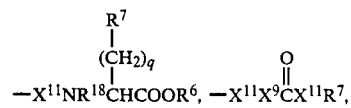

NH(CH$_2$)$_{2-3}$—NHCOR$^7$, NH(CH$_2$)$_{2-3}$—NHR$^7$

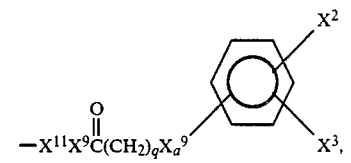

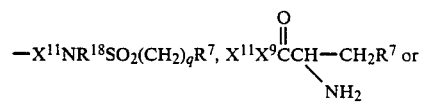

R$^4$ and R$^5$ are independently R$^6$ or in combination with the N of the NR$^4$R$^5$ group form an unsubstituted or mono or disubstituted, saturated or unsaturated, 4–7 membered heterocyclic ring, or benzofused 4–7 membered heterocyclic ring or said heterocyclic ring or said benzofused heterocyclic ring which further comprises a second heteroatom selected from O and NCH$_3$ and the substituent(s) is/are independently selected from C$_{1-4}$alkyl;

R$^6$ is H, loweralkyl, cycloloweralkyl, substituted or unsubstituted phenyl, or substituted or unsubstituted phenylloweralkyl (wherein the substituents are 1 or 2 of halo, loweralkyl, loweralkoxy, nitro, or CF$_3$);

$R^7$ is a α- or β-naphthyl, substituted or unsubstituted phenyl (wherein the substituents are 1 to 2 of halo, $-NO_2$, $-OH$, $-X^{11}-NR^4R^5$, loweralkyl, loweralkoxy, $CF_3$, loweralkylthio, cyano, phenyl, acetylamino, acetoxy, $SCF_3$, $C\equiv CH$, $CH_2SCF_3$, $OCHF_2$, SH or thio-phenyl) 2-, 3-, 4-pyridyl,

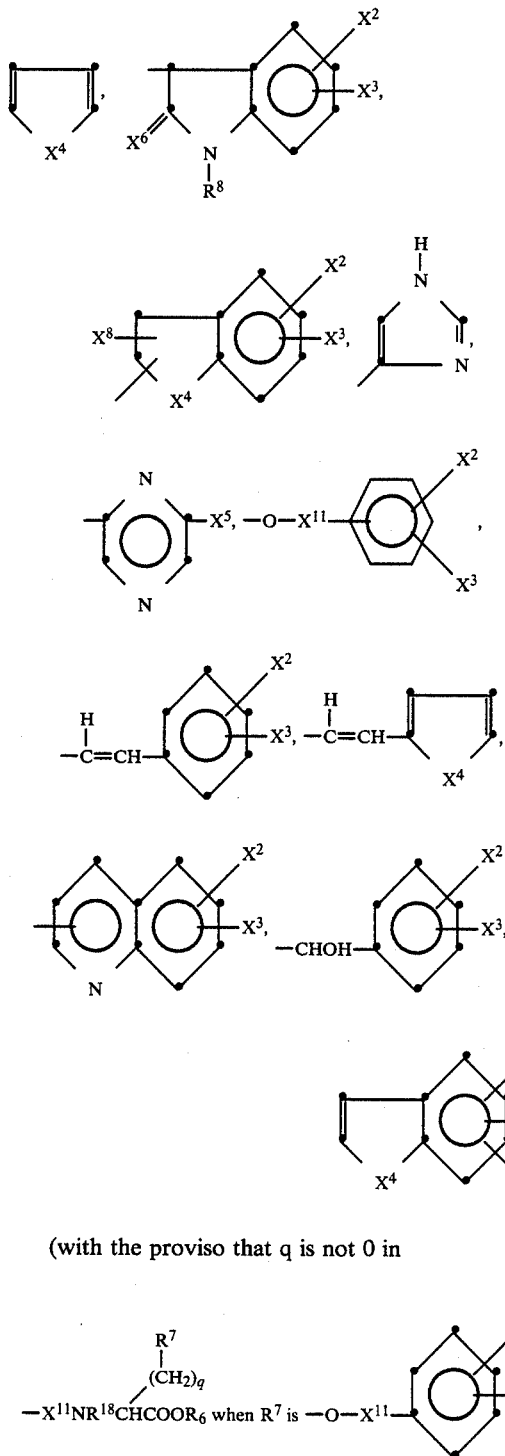

(with the proviso that q is not 0 in

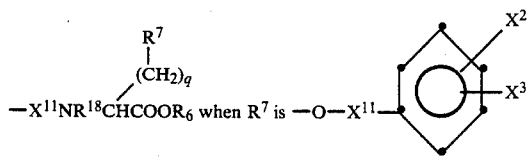

$-X^{11}NR^{18}CHCOOR_6$ when $R^7$ is $-O-X^{11}$—

$R^8$ is H, loweralkyl, cycloloweralkyl, $-X^{12}CONH_2$, $-X^{12}COOR^6$, $-X^{11}$—cycloloweralkyl,

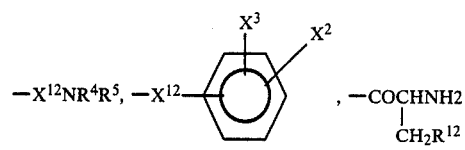

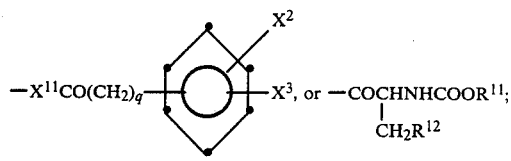

$R^{11}$ and $R^{12}$ are independently loweralkyl or cycloloweralkyl;

$R^{13}$ is O;

$R^{14}$ is loweralkyl or phenylloweralkyl;

$R^{16}$ and $R^{17}$ are, when separate, independently H, loweralkyl, lower alkenyl, $-X^{11}$cycloloweralkyl, $-X^{12}-NR^4R^5, X^{12}CONR^4R^5, -X^{12}C\equiv N$,

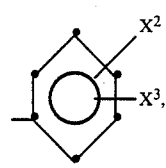

$-X^{12}COOR^6$, or $-CN$; or, when joined, form with N, a heterocycle

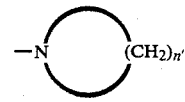

wherein n' is 2–6;

$R^{18}$ is H or loweralkyl;

p is 0 or 1;

q is 0–4;

r is 1 or 2;

$X^1$ is H, $-NO_2$, $CF_3$ CN, OH, loweralkyl, halo, loweralkylthio, loweralkoxy, $-X^{11}COOR^6$ or $-X^{11}NR^4R^5$;

$X^2$ and $X^3$ are independently H, $-OH$, $-NO_2$, halo, loweralkylthio, loweralkyl or loweralkoxy;

$X^4$ is S, O, $CH_2$ or $NR^8$;

$X^5$ is H, $CF_3$, CN, $COOR^6$, $NO_2$, or halo;

$X^6$ is O or HH;

$X^8$ is H or loweralkyl;

$X^9$ and $X^9$ are independently $NR^{18}$, O;

$X^{11}$ is absent or $C_{1-4}$ linear or branched alkylene;

$X^{12}$ is $C_{1-4}$ linear or branched alkylene.

and the pharmaceutically acceptable salts thereof.

2. A compound of claim 1 wherein:

$R^1$ is $-NR^{16}R^{17}$;

$R^2$ is substituted or unsubstituted phenyl (wherein the substituents are 1 or 2 of halo, loweralkyl, loweralkoxy, carboxyl, carboxyloweralkyl, nitro, $-CF_3$, or hydroxy), 2-, 3-, 4-pyridyl $-X^{12}COOR^6$ or or

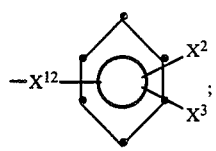

R³ is

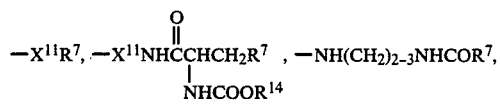

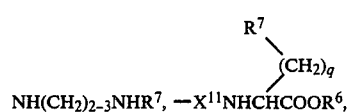

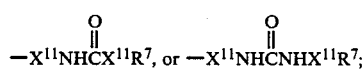

R⁴ and R⁵ are independently H or loweralkyl;
R⁶ is H or loweralkyl;
R⁷ is α- or β-naphthyl,

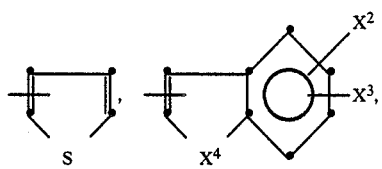

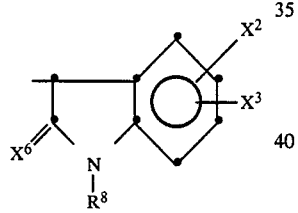

substituted or unsubstituted phenyl (wherein the substituents are 1 to 2 of halo, —NO₂, —OH, —X¹¹NR⁴R⁵, loweralkyl, CF₃, loweralkoxy, loweralkylthio, CN, C≡CH, SCF₃, OCHF₂, or thiophenyl),

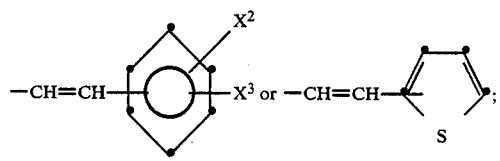

R⁸ is H, loweralkyl or

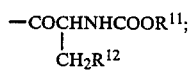

R¹¹ and R¹² are independently loweralkyl;
R¹⁴ is loweralkyl;
R¹⁶ and R¹⁷ are independently H, loweralkyl, —X¹¹cycloloweralkyl, —X¹²NR⁴R⁵, —X¹²CONR⁴R⁵, —X¹²CN,

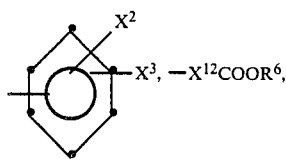

or —CN;
q is 0–4;
r is 1 or 2;
X¹ is H, —NO₂, CF₃, CN, OH, loweralkyl, halo, loweralkylthio, loweralkoxy, —X¹¹COOR⁶, or —X¹¹NR⁴R⁵;
X² and X³ are independently H, —OH, —NO₂, halo, loweralkylthio, loweralkyl, or loweralkoxy;
X⁴ is S, O, or NR⁸;
X⁶ is O or HH;
and the pharmaceutically acceptable salts thereof.

3. A compound of claim 2 wherein:
R¹ is —NR¹⁶R¹⁷;
R² is substituted or unsubstituted phenyl (wherein the substituents are 1 or 2 of halo or carboxyl) or —(CH₂)₁₋₂COOR⁶;
R³ is

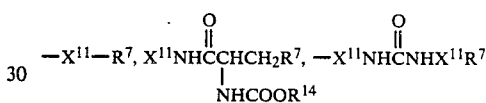

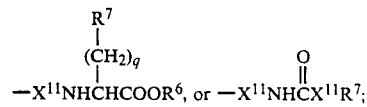

R⁶ is H or loweralkyl;
R⁷ is α- or β-naphthyl,

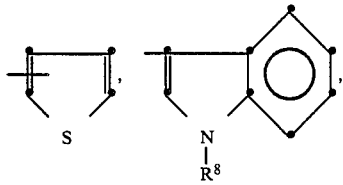

substituted phenyl (wherein the substituents are 1 or 2 of halo, loweralkyl, loweralkoxy, or CF₃), or

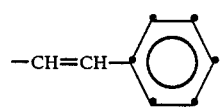

R⁸ is H, methyl, or ethyl;
R¹⁴ is t-butyl;

$R^{16}$ and $R^{17}$ are independently H, loweralkyl, —CN, —$X^{11}$cycloloweralkyl, $X^{12}NR^4R^5$, —$X^{12}CONR^4R^5$, —$X^{12}CN$;

q is 0–4;

r is 1 or 2;

$X^1$ is H, —$NO_2$, $CF_3$ CN, OH, or halo;

$X^2$ and $X^3$ are independently H, —OH, —$NO_2$, loweralkyl or halo;

and the pharmaceutically acceptable salts thereof.

4. A compound of claim 3 wherein:

$R^1$ is —$NH_2$, —$NH(CH_2)_{0-2}CH_3$, $NHCH_2COOH$, —NHCN,

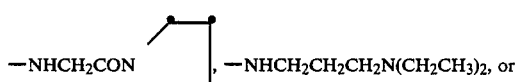, 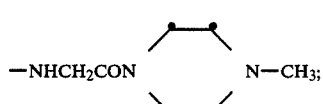

$R^2$ is phenyl, o-fluorophenyl, o-chlorophenyl, p-fluorophenyl, p-chlorophenyl, 2,6-difluorophenyl, —$CH_2COOEt$, —$CH_2COO$—t—Bu, o-carboxyphenyl, —$CH_2CH_2COOEt$, or —$CH_2CH_2COOt$—Bu;

$R^3$ is —$(CH_2)_{1-2}R^7$,

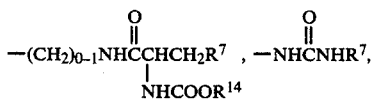, 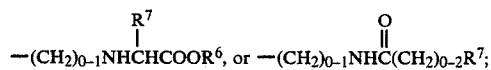

and the stereochemistry relates to D-tryptophan when $R^3$ is linked to the 7-membered ring via a methylene group;

$R^6$ is H, methyl or ethyl;

$R^7$ is α- or β-naphthyl, mono- or dihalophenyl, mono- or dimethylphenyl, methoxyphenyl,

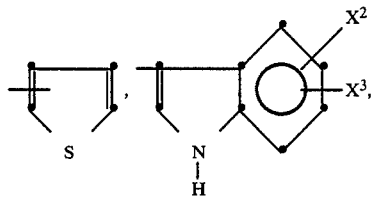

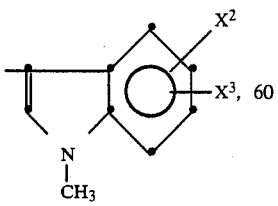

$R^{14}$ is t-butyl;

r is 1;

$X^1$ is H, chloro, fluoro, or nitro;

$X^2$ and $X^3$ are independently H, —OH, fluoro or chloro or methyl or ethyl;

and the pharmaceutically acceptable salts thereof.

5. A compound of claim 1 which is
2-Phenylamino-3(R)-(3'-indolyl)methyl-5-(2'-fluorophenyl)-2H-1,4-benzodiazepine;
2-Amino-3(R)-(3'-indolyl)methyl-5-(2'-fluorophenyl)-2H-1,4-benzodiazepine;
2-Methylamino-3(R)-(3'-indolyl)methyl-5-(2'-fluorophenyl)-2H-1,4-benzodiazepine;
N-[3-(((4-Chlorophenyl)aminocarbonyl)amino)-5-phenyl-3H-1,4-benzodiazepin-2-yl]-glycine;
N-[3-(((4-Chlorophenyl)aminocarbonyl)amino)-5-phenyl-3H-1,4-benzodiazepin-2-yl]-glycine ethyl ester;
2-Ethoxycarbonylmethylamino-3(R)-(3'-indolyl)methyl-5-(2'-fluorophenyl)-2H-1,4-benzodiazepine;
2-Cyanoamino-3(R)-(3'-indolyl)methyl-5-(2'-fluorophenyl)-2H-1,4-benzodiazepine;
2-n-Propylamino-3(R)-(3'-indolyl)methyl-5-(2'-fluorophenyl)-2H-1,4-benzodiazepine; and
2-Carboxymethylamino-3(R)-(3'-indolyl)methyl-5-(2'-fluorophenyl)-2H-1,4-benzodiazepine.

6. A pharmaceutical composition useful for treating gastrointestinal disorders, central nervous system disorders, or regulating appetite in mammals, comprising a pharmaceutically effective amount of a compound of Formula I of claim 1 and an acceptable pharmaceutical carrier.

7. A pharmaceutical composition of claim 6 useful for treating gastrointestinal disorders, central nervous system disorders, or regulating appetite in mammals, comprising a pharmaceutically effective amount of a compound of Formula I wherein:

$R^1$ is —$NR^{16}R^{17}$;

$R^2$ is substituted or unsubstituted phenyl (wherein the substituents are 1 or 2 of halo, loweralkyl, loweralkoxy, carboxyl, carboxyloweralkyl, nitro, —$CF_3$, or hydroxy), 2-, 3-, 4-pyridyl —$X^{12}COOR^6$ or

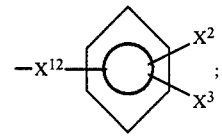

$R^3$ is

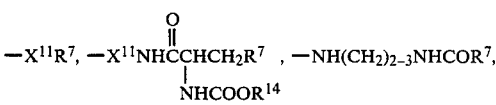

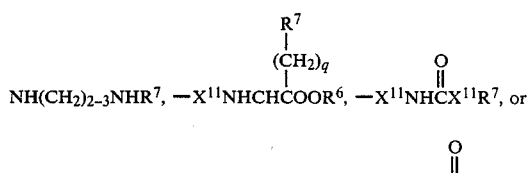

$R^4$ and $R^5$ are independently H or loweralkyl;

$R^6$ is H or loweralkyl;

$R^7$ is α- or β-naphthyl,

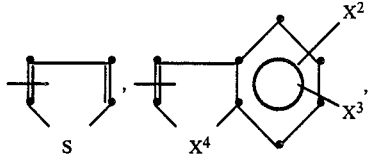

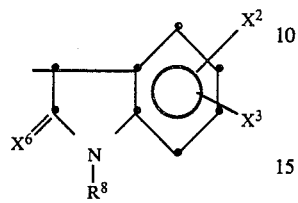

substituted or unsubstituted phenyl (wherein the substituents are 1 to 2 of halo, —NO$_2$, —OH, —X$^{11}$NR$^4$R$^5$, loweralkyl, CF$_3$, loweralkoxy, loweralkylthio, CN, C≡CH, SCF$_3$, OCHF$_2$, or thiophenyl),

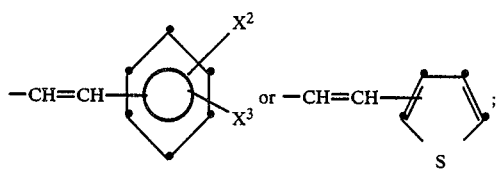

R$^8$ is H, loweralkyl or

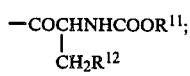

R$^{11}$ and R$^{12}$ are independently loweralkyl;
R$^{14}$ is loweralkyl;
R$^{16}$ and R$^{17}$ are independently H, loweralkyl, —X$^{11}$cycloloweralkyl, —X$^{12}$NR$^4$R$^5$, —X$^{12}$CONR$^4$R$^5$, —X$^{12}$CN,

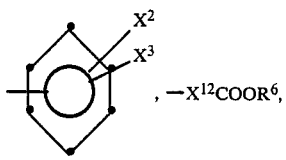

or —CN;
q is 0–4;
r is 1 or 2;
X$^1$ is H, —NO$_2$, CF$_3$, CN, OH, loweralkyl, halo, loweralkylthio, loweralkoxy, —X$^{11}$COOR$^6$, or —X$^{11}$NR$^4$R$^5$;
X$^2$ and X$^3$ are independently H, —OH, —NO$_2$, halo, loweralkylthio, loweralkyl, or loweralkoxy;
X$^4$ is S, O, or NR$^8$;
X$^6$ is O or HH;
and the pharmaceutically acceptable salts thereof.

8. A method of treating gastrointestinal disorders, central nervous system disorders, or regulating appetite in mammals which comprises administering to said mammals a pharmaceutically effective amount of a compound of Formula I of claim 1.

9. A method of claim 8 of treating gastrointestinal disorders in humans which comprises administering a pharmaceutically effective amount of a compound of Formula I wherein:

R$^1$ is —NR$^{16}$R$^{17}$;

R$^2$ is substituted or unsubstituted phenyl (wherein the substituents are 1 or 2 of halo, loweralkyl, loweralkoxy, carboxyl, carboxyloweralkyl, nitro, —CF$_3$, or hydroxy), 2-, 3-, 4-pyridyl —X$^{12}$COOR$^6$ or or

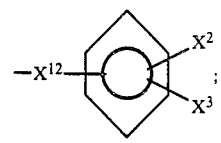

R$^3$ is

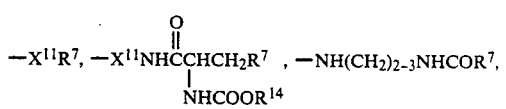

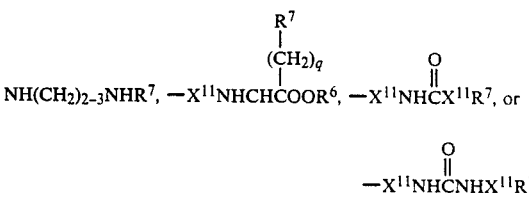

R$^4$ and R$^5$ are independently H or loweralkyl;
R$^6$ is H or loweralkyl;
R$^7$ is α- or β-naphthyl,

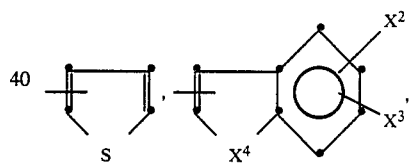

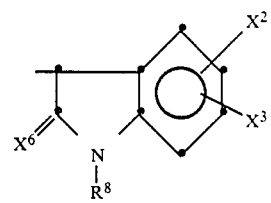

substituted or unsubstituted phenyl (wherein the substituents are 1 to 2 of halo, —NO$_2$, —OH, —X$^{11}$NR$^4$R$^5$, loweralkyl, CF$_3$, loweralkoxy, loweralkylthio, CN, C≡CH, SCF$_3$, OCHF$_2$, or thiophenyl),

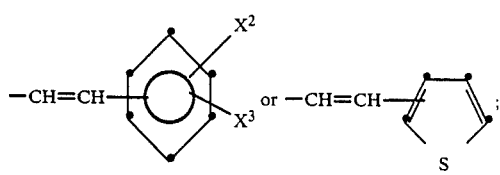

R$^8$ is H, loweralkyl or

—COCHNHCOOR$^{11}$;
|
CH$_2$R$^{12}$

R$^{11}$ and R$^{12}$ are independently loweralkyl;

R$^{14}$ is loweralkyl;

R$^{16}$ and R$^{17}$ are independently H, loweralkyl,

—X$^{11}$cycloloweralkyl, —X$^{12}$NR$^4$R$^5$,

—X$^{12}$CONR$^4$R$^5$, —X$^{12}$CN,

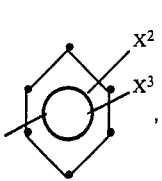

—X$^{12}$COOR$^6$, or —CN;
q is 0–4;
r is 1 or 2;
X$^1$ is H, —NO$_2$, CF$_3$, CN, OH, loweralkyl, halo, loweralkylthio, loweralkoxy, —X$^{11}$COOR$^6$, or —X$^{11}$NR$^4$R$^5$;
X$^2$ and X$^3$ are independently H, —OH, —NO$_2$, halo, loweralkylthio, loweralkyl, or loweralkoxy;
X$^4$ is S, O, or NR$^8$;
X$^6$ is O or HH;
and the pharmaceutically acceptable salts thereof.

* * * * *